(12) United States Patent
Bonaventure et al.

(10) Patent No.: US 7,728,107 B2
(45) Date of Patent: Jun. 1, 2010

(54) CANINE 5-HYDROXYTRYPTAMINE 2A AND 2B RECEPTOR

(75) Inventors: Pascal Bonaventure, San Diego, CA (US); Changlu Liu, San Diego, CA (US); Timothy W. Lovenberg, San Diego, CA (US); Diane Nepomuceno, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 124 days.

(21) Appl. No.: 11/795,278

(22) PCT Filed: Jan. 13, 2006

(86) PCT No.: PCT/US2006/002644

§ 371 (c)(1),
(2), (4) Date: Jul. 12, 2007

(87) PCT Pub. No.: WO2006/076741

PCT Pub. Date: Apr. 20, 2006

(65) Prior Publication Data

US 2008/0131913 A1 Jun. 5, 2008

Related U.S. Application Data

(60) Provisional application No. 60/644,423, filed on Jan. 14, 2005.

(51) Int. Cl.
*C07K 14/705* (2006.01)
(52) U.S. Cl. .................................................. 530/350
(58) Field of Classification Search ....................... None
See application file for complete search history.

(56) References Cited

U.S. PATENT DOCUMENTS 5,360,735 A 11/1994 Weinshank et al.
5,661,024 A * 8/1997 Kao et al. .................... 435/356

OTHER PUBLICATIONS

Adner et al., "An Assay to Evaluate the Long-Term Effects of Inflammatory Mediators on Murine Airway Smooth Muscle: Evidence that TNFα Up-Regulates 5-HT$_{2A}$-Mediated Contraction", *Br J Pharmacol.*, 2002, vol. 137, pp. 971-982.
Aubert et al., "5-HT$_2$Receptor Gene Polymorphism is Associated with Food and Alcohol Intake in Obese People", *Int J Obes.*, 2000, vol. 24, pp. 920-924.
Baluta et al., "Renin-Angiotensin-Aldosterone System Inhibition in Prevention of Diabetes Mellitus", *Rom J Intern Med.*, 2004, vol. 42(2), pp. 277-288.
Bhatnagar et al., "Caveolin-1 Interacts with 5-HT$_{2A}$ Serotonin Receptors and Profoundly Modulates the Signaling of Selected Gα$_q$-coupled Protein Receptors", *J Biol Chem.*, 2004, vol. 279(33), pp. 34614-34623.
Boehme et al., "Cutting Edge: Serotonin is a Chemotactic Factor for Eosinophils and Functions Additively with Eotaxin", *J Immunol.*, 2004, vol. 173, pp. 3599-3603.
Bonaventure et al., "Nuclei and Subnuclei Gene Expression Profiling in Mammalian Brain", *Brain Res.*, 2002, vol. 943, pp. 38-47.
Bush, "Effects of the Serotonin Antagonists, Cyproheptadine, Ketanserin and Mianserin, on Cyclic Flow Reductions in Stenosed Canine Coronary Arteries", *J Pharmacol Exp Ther.*, 1987, vol. 240(2), pp. 674-682.
Cazzola et al., "Effect of the Selective 5-HT$_2$ Antagonist Ketanserin on Adenosine-Induced Bronchoconstriction in Asthmatic Subjects", *Immunopharmacology*, 1992, vol. 23, pp. 21-28.
Celada et al., "The Therapeutic Role of 5-HT$_{1A}$ and 5-HT$_{2A}$ Receptors in Depression", *J Psychiatry Neurosci.*, 2004, vol. 29(4), pp. 252-265.
Cohen et al., "Evidence for 5-HT$_2$ Receptors Mediating Contraction in Vascular Smooth Muscle", *J Pharmacol Exp Ther.*, 1981, vol. 218(2), pp. 421-425.
De Chaffoy de Courcelles et al., "Evidence that Phospholipid Turnover is the Signal Transducing System Coupled to Serotonin-S$_2$ Receptor Sites", *J Biol Chem.*, 1985, vol. 260(12), pp. 7603-7608.
Du et al., "Association of Polymorphism of Serotonin 2A Receptor Gene with Suicidal Ideation in Major Depressive Disorder", *Am J Med Genet.*, 2000, vol. 96, pp. 56-60.
Duxon et al., "Evidence for Expression of the 5-Hydroxytryptamine-2B Receptor Protein in the Rat Central Nervous System", *Neuroscience*, 1997, vol. 76(2), pp. 323-329.
Fitzgerald et al., "High-Affinity Agonist Binding Correlates with Efficacy (Intrinsic Activity) at the Human Serotonin 5-HT$_{2A}$ and 5-HT$_{2C}$ Receptors: Evidence Favoring the Ternary Complex and Two-State Models of Agonist Action", *J Neurochem.*, 1999, vol. 72(5), pp. 2127-2134.
Foguet et al., "Cloning and Functional Characterization of the Rat Stomach Fundus Serotonin Receptor", *EMBO J.*, 1992, vol. 11(9), pp. 3481-3487.
Fonseca et al., "Distribution of Serotonin 2A, 2C, and 3 receptor mRNA in Spinal Cord and Medulla Oblongata", *Brain Res Mol Brain Res.*, 2001, vol. 89, pp. 11-19.
Giles et al., "Characterization of a 5-HT1B Receptor on CHO Cells: Functional Responses in the Absence of Radioligand Binding", *Br J Pharmacol.*, 1996, vol. 117, pp. 1119-1126.
Gonzales et al., "Hypoprolactinemia as Related to Seminal Quality and Serum Testosterone", *Arch Androl.*, 1989, vol. 23, pp. 259-265.
Hall et al., "Autoradiographic Localization of 5-HT$_{2A}$ Receptors in the Human Brain Using [$^3$H]M100907 and [$^{11}$C]M100907", *Synapse*, 2000, vol. 38, pp. 421-431.
Hoyer et al., "Molecular, Pharmacological and Functional Diversity of 5-HT Receptors", *Pharmacol Biochem Behav.*, 2002, vol. 71, pp. 533-554.

(Continued)

*Primary Examiner*—Michael Pak

(57) ABSTRACT

Canine 5-hydroxytryptamine 2 receptor materials are described, including polypeptides corresponding to SEQ ID NOs.:8 and 10 and polynucleotides expressing them corresponding to SEQ ID NOs.:7 and 9. Such materials are useful as reagents in drug screening assays to identify compounds having 5-HT$_2$ receptor-modulating activity.

1 Claim, 25 Drawing Sheets

OTHER PUBLICATIONS

Huang et al., "Ultrastructural Localization of Serotonin 2A and N-Methyl-D-Aspartate Receptors in Somata and Dendrites of Single Neurons within Rat Dorsal Motor Nucleus of the Vagus", *J Comp Neurol.*, 2003, vol. 455, pp. 270-280.

Jara et al., "Prolactin in Human Systemic Lupus Erythematosus", *Lupus*, 2001, vol. 10, pp. 748-756.

Jerman et al., "Pharmacological Characterisation of Human $5-HT_2$ Receptor Subtypes", *Eur J Pharmacol.*, 2001, vol. 414, pp. 23-30.

Kantor et al., "Increased Wakefulness, Motor Activity and Decreased Theta Activity After Blockade of the $5-HT_{2B}$ Receptor by the Subtype-Selective Antagonist SB-215505", *Br J Pharmacol.*, 2004, vol. 142, pp. 1332-1342.

Kroeze et al., "Molecular Biology of Serotonin Receptors-Structure and Function at the Molecular Level", *Curr Top Med Chem.*, 2002, vol. 2, pp. 507-528.

Kursar et al., "Molecular Cloning, Functional Expression, and Pharmacological Characterization of a Novel Serotonin Receptor (5-Hydroxytryptamine$_{2F}$) from Rat Stomach Fundus", *Mol Pharmacol.*, 1992, vol. 42, pp. 549-557.

Leysen, "$5-HT_2$ Receptors", *Curr Drug Targets—CNS Neurol Disord.*, 2004, vol. 3, pp. 11-26.

Massou et al., "Frontal $5-HT_{2A}$ Receptors Studied in Depressive Patients During Chronic Treatment by Selective Serotonin Reuptake Inhibitors", *Psychopharmacology*, 1997, vol. 133, pp. 99-101.

Masuda et al., "Sequencing of Canine 5-Hydroxytriptamine Receptor (5-HTR) 1B, 2A, 2C Genes and Identification of Polymorphisms in the 5-HTR1B Gene", *J Vet Med Sci.*, 2004, vol. 66(8), pp. 965-972.

Meltzer, "The Role of Serotonin in Antipsychotic Drug Action", *Neuropsychopharmacology*, 1999, vol. 21(2S), pp. 106S-115S.

Meyer et al., "The Effects of Single Dose Nefazodone and Paroxetine upon $5-HT_{2A}$ Binding Potential in Humans using [$^{18}$F]-setoperone PET", *Psychopharmacology*, 1999, vol. 144, pp. 279-281.

Ogawa et al., "Effects of R-10244, an Orally Active $5-HT_{2A}$ Receptor Antagonist, in Rat Models of Peripheral Vascular Disease", *Vascul Pharmacol.*, 2004, vol. 41, pp. 7-13.

Pazos et al., "Mesulergine, A Selective Serotonin-2 Ligand in the Rat Cortex, Does Not Label These Receptors in Porcine and Human Cortex: Evidence for Species Differences in Brain Serotonin-2 Receptors", *Eur J Pharmacol.*, 1985, vol. 106, pp. 531-538.

Pazos et al., "The Binding of Serotonergic Ligands to the Porcine Choroid Plexus: Characterization of a New Type of Serotonin Recognition Site", Eur J Pharmacol., 1985, vol. 106, pp. 539-546.

Prins et al., "Characterization of the Receptors Involved in the 5-HT-Induced Excitation of Canine Antral Longitudinal Muscle", *Br J Pharmacol.*, 2001, vol. 134, pp. 1351-1359.

Porter et al., "Functional Characterization of Agonists at Recombinant Human $5-HT_{2A}$, $5-HT_{2B}$ and $5-HT_{2C}$ Receptors in CHO-K1 cells", *Br J Pharmacol.*, 1999, vol. 128, pp. 13-20.

Rinaldi-Carmona et al., "Biochemical and Pharmacological Properties of SR 46349B, A New Potent and Selective 5-Hydroxytryptamine$_2$ Receptor Antagonist", *J Pharmacol Exp Ther.*, 1992, vol. 262(2), pp. 759-768.

Rittenhouse et al., "Evidence that the Serotonin Agonist, DOI, Increases Renin Secretion and Blood Pressure Through both Central and Peripheral $5-HT_2$ Receptors", *J Pharmacol Exp Ther.*, 1991, vol. 259(1), pp. 58-65.

Rittenhouse et al., "Evidence that ACTH Secretion is Regulated by Serotonin$_{2A/2C}$ ($5-HT_{2A/2C}$) Receptors", *J Pharmacol Exp Ther.*, 1994, vol. 271(3), pp. 1647-1655.

Roth et al., "5-Hydroxytryptamine$_2$-Family Receptors (5-Hydroxytryptamine$_{2A}$, 5-Hydroxytryptamine$_{2B}$, 5-Hydroxytryptamine$_{2C}$): Where Structure Meets Function", *Pharmacol Ther.*, 1998, vol. 79(3), pp. 231-257.

Saucier et al., "Identification of an Endogenous 5-Hydroxytryptamine$_{2A}$ Receptor in NIH-3T3 Cells: Agonist-Induced Down-Regulation Involves Decreases in Receptor RNA and Number", *J Neurochem.*, 1997, vol. 68(5), pp. 1998-2011.

Saydoff et al., "Enhanced Serotonergic Transmission Stimulates Oxytocin Secretion in Conscious Male Rats", *J Pharmacol Exp Ther.*, 1991, vol. 257(1), pp. 95-99.

Schechter et al., "1-(2,5-Dimethoxy-4-Iodophenyl)-2-Aminopropane (DOI) Exerts an Anorexic Action that is Blocked by $5-HT_2$ Antagonists in Rats", *Psychopharmacology*, 1988, vol. 94, pp. 342-346.

Schmidt et al., "Therapeutic Effects of Angiotensin ($AT_1$) Receptor Antagonists", *Am J Cardiovasc Drugs*, 2004, vol. 4(6), pp. 361-368.

Schmuck et al., "Activation of Meningeal $5-HT_{2B}$ Receptors: An Early Step in the Generation of Migraine Headache?", *Eur J Neurosci.*, 1996, vol. 8, pp. 959-967.

Schreiber et al., "(1-(2,5-Dimethoxy-4 Iodophenyl)-2-Aminopropane)-Induced Head-Twitches in the Rat are Mediated by 5-Hydroxytryptamine ($5-HT)_{2A}$ Receptors: Modulation by Novel $5-HT_{2A/2C}$ Antagonists, $D_1$ Antagonists and $5-HT_{1A}$ Agonists," *J Pharmacol Exp Ther.*, 1995, vol. 273(1), pp. 101-112.

Sethi et al., "Changes in β-adrenoceptors in Heart Failure Due to Myocardial Infarction are Attenuated by Blockade of Renin-Angiotensin System", *Mol Cell Biochem.*, 2004, vol. 263, pp. 11-20.

Shoji et al., "Renal Vasodilatation Induced by DOI, a $5-HT_2$ Receptor Agonist, in the Canine Kidney", *Eur J Pharmacol.*, 1990, vol. 190, pp. 247-250.

Sorensen et al., "Characterization of the 5-HT2 Receptor Antagonist MDL 100907 as a Putative Atypical Antipsychotic: Behavioral, Electrophysiological and Neurochemical Studies", *J Pharmacol Exp Ther.*, 1993, vol. 266(2), pp. 684-691.

Steward et al., "The Atypical Antipsychotic Drug Clozapine Enhances Chronic PCP-Induced Regulation of Prefrontal Cortex $5-HT2_A$ Receptors", *Neuropharmacology*, 2004, vol. 47, pp. 527-537.

Ufearo et al., "Restoration of Normal Sperm Characteristics in Hypoprolactinemic Infertile Men Treated with Metoclopramide and Exogenous Human Prolactin", *Clin Pharmacol Ther.*, 1995, vol. 58(3), pp. 354-359.

Van de Kar et al., "$5-HT_{2A}$Receptors Stimulate ACTH, Corticosterone, Oxytocin, Renin, and Prolactin Release and Activate Hypothalamic CRF and Oxytocin-Expressing Cells", *J Neurosci.*, 2001, vol. 21(10), pp. 3572-3579.

Wainscott et al., "Pharmacologic Characterization of the Human 5-Hydroxytryptamine2B Receptor: Evidence for Species Differences", *J Pharmacol Exp Ther.*, 1996, vol. 276(2), pp. 720-727.

\* cited by examiner

Figure 1A

```
                  *10        *20        *30        *40        *50        *60        *70
Dog:        MDVLFEDNAPLSPTTSSLMPSNGDPRLYGNDLNAGDANTSDAFNWTVDAENRTNLSCEGCLSPPCFSLLH
Consensus:  MD:L E:N::LS:TT:SLM. N:D.RLY:ND:N:G:ANTSDAFNWTVD:ENRTNLSCEGCLSP:C:SLLH
Human:      MDILCEENTSLSSTTNSLMQLNDDTRLYSNDFNSGEANTSDAFNWTVDSENRTNLSCEGCLSPSCLSLLH
                  *10        *20        *30        *40        *50        *60        *70
```

Figure 1B

```
              *80        *90       *100       *110       *120       *130      *140
Dog:      LQEKNWSALLTAVVIILTIAGNILVIMAVSLEKKLQNATNYFLMSLAIADMLLGFLVMPVSMLTILYGYR
Consensus: LQEKNWSALLTAVVIILTIAGNILVIMAVSLEKKLQNATNYFLMSLAIADMLLGFLVMPVSMLTILYGYR
Human:    LQEKNWSALLTAVVIILTIAGNILVIMAVSLEKKLQNATNYFLMSLAIADMLLGFLVMPVSMLTILYGYR
              *80        *90       *100       *110       *120       *130      *140
                              TM1                              TM2
```

Figure 1C

```
              *150       *160       *170       *180       *190       *200       *210
Dog:       WPLPSKLCAVWIYLDVLFSTASIMHLCAISLDRYVAIQNPIHHSRFNSRTKAFLKIIAVWTISVGISMPI
Consensus: WPLPSKLCAVWIYLDVLFSTASIMHLCAISLDRYVAIQNPIHHSRFNSRTKAFLKIIAVWTISVGISMPI
Human:     WPLPSKLCAVWIYLDVLFSTASIMHLCAISLDRYVAIQNPIHHSRFNSRTKAFLKIIAVWTISVGISMPI
              *150       *160       *170       *180       *190       *200       *210
                            TM3                                      TM4
```

Figure 1D

```
             *220          *230          *240          *250          *260          *270         *280
Dog:      PVFGLQDDSKVFKEGSCLLADDNFVLIGSFVSFFIPLTIMVITYFLTIKSLQKEATLCVSDPGTRAKLAS
Consensus: PVFGLQDDSKVFKEGSCLLADDNFVLIGSFVSFFIPLTIMVITYFLTIKSLQKEATLCVSD GTRAKLAS
Human:    PVFGLQDDSKVFKEGSCLLADDNFVLIGSFVSFFIPLTIMVITYFLTIKSLQKEATLCVSDLGTRAKLAS
             *220          *230          *240          *250          *260          *270         *280
          TM4                                            TM5
```

Figure 1E

```
              *290       *300       *310       *320       *330       *340      *350
Dog:      FSFLPQSSLSSEKLFQRSIHREPGSY-GRRTMQSISNEQKACKVLGIVFFLFVVMWCPFFITNIMAVICK
Consensus: FSFLPQSSLSSEKLFQRSIHREPGSY GRRTMQSISNEQKACKVLGIVFFLFVVMWCPFFITNIMAVICK
Human:    FSFLPQSSLSSEKLFQRSIHREPGSYTGRRTMQSISNEQKACKVLGIVFFLFVVMWCPFFITNIMAVICK
              *290       *300       *310       *320       *330       *340      *350
                                                   TM6
```

Figure 1F

```
              *360       *370       *380       *390       *400       *410
Dog:       ESCNEDIIGALLNVFVWIGYLSSAVNPLVYTLFNKTYRSAFSRYIQCQYKENKKPLQLILVNTIPALAYK
Consensus: ESCNED:IGALLNVFVWIGYLSSAVNPLVYTLFNKTYRSAFSRYIQCQYKENKKPLQLILVNTIPALAYK
Human:     ESCNEDVIGALLNVFVWIGYLSSAVNPLVYTLFNKTYRSAFSRYIQCQYKENKKPLQLILVNTIPALAYK
              *360       *370       *380       *390       *400       *410       *420
                                         TM7
```

Figure 1G

```
            *420       *430       *440       *450       *460       *470
Dog:       SSQLQMGQKKNSKKDAKSTDNDYSMVALGKQHSEDAPTDNINTVNEKVSCV
Consensus: SSQLQMGQKKNSK:DAK:TDND.SMVALGKQHSE:A:.DN :.VNEKVSCV
Human:     SSQLQMGQKKNSKQDAKTTDNDCSMVALGKQHSEEASKDNSDGVNEKVSCV
            *420       *430       *440       *450       *460       *470
```

Figure 2A

```
              *10         *20         *30         *40         *50         *60         *70
Dog:       MAISYRISE-QSTIPEHILQSSFHHLIFANWSGLQTESIPEEMKQTGEQQGKKPQWAALLLTVIIPTIGG
Consensus: MA:SYR:SE QSTIPEHILQS:F H:I :NWSGLQTESIPEEMKQ. E:QG:K :WAALLIL VIIPTIGG
Human:     MALSYRVSELQSTIPEHILQSTFVHVISSNWSGLQTESIPEEMKQIVEEQGNKLHWAALLLMVIIPTIGG
              *10         *20         *30         *40         *50         *60         *70
                                                                              TM1
```

Figure 2B

```
                    *80        *90       *100       *110       *120       *130       *140
Dog:       NILVILAISLEKKLQYATNYFLMSLAVADLLVGLFVMPIALLTIMFETIWPLPLVLCPAWLFLDVLFST
Consensus: N.LVILA:SLEKKLQYATNYFLMSLAVADLLVGLFVMPIALLTIMFE::WPLPLVLCPAWLFLDVLFST
Human:     NTLVILAVSLEKKLQYATNYFLMSLAVADLLVGLFVMPIALLTIMFEAMWPLPLVLCPAWLFLDVLFST
                *80        *90       *100       *110       *120       *130
               TM1                       TM2                        TM3
```

Figure 2C

```
             *140       *150       *160       *170       *180       *190       *200       *210
      Dog: ASIMHLCAISVDRYIAIKKPIQANQSNSRATAFIKITVVWLISIGIAIPVPIRGIETDRSNPSNITCVLTK
Consensus: ASIMHLCAISVDRYIAIKKPIQANQ NSRATAFIKITVVWLISIGIAIPVPI :GIETD  .NP:NITCVLTK
    Human: ASIMHLCAISVDRYIAIKKPIQANQYNSRATAFIKITVVWLISIGIAIPVPIKGIETDVDNPNNITCVLTK
             *150       *160       *170       *180       *190       *200       *210
              TM3                                  TM4
```

Figure 2D

```
              *220        *230        *240        *250        *260        *270
Dog:       DRFGNFMLYGSLAAFFTPLAIMIVTYFLTIRALQKKASLVKNKPPPCLTWLTVSTAFRRNETPCSSPEK   *280
Consensus: :RFG:FML:GSLAAFFTPLAIMIVTYFLTI:ALQKKA LVKNKPP. LTWLTVST.F:R:ETPCSSPEK
Human:     ERFGDFMLFGSLAAFFTPLAIMIVTYFLTIHALQKKAYLVKNKPPQRLTWLTVSTVFQRDETPCSSPEK
                            TM5
              *220        *230        *240        *250        *260        *270
```

Figure 2E

```
           *280       *290       *300       *310       *320       *330       *340       *350
      Dog: VAMLDGSHKDRTLPSSSDDLLMRRRMSTAGKKSMQTISNEQRASKVLGIVFFLFLLMWCPFFITNVTLVLCD
Consensus: VAMLDGS:KD::LP::S:D: LMRR ST GKKS:QTISNEQRASKVLGIVFFLFLLMWCPFFITN:TLVLCD
    Human: VAMLDGSRKDKALPNSGDETLMRRTSTIGKKSVQTISNEQRASKVLGIVFFLFLLMWCPFFITNITLVLCD
           *280       *290       *300       *310       *320       *330       *340       *350
                                                                 TM6
```

Figure 2F

```
              *360      *370      *380      *390      *400      *410
Dog:      SCNQTTLNMLLEVFVWIGYVSSGVNPLVYTLFNKTFRNAFGRYITCNYQAMKSVKTVRKCSSNNYFRNG
Consensus: SCNQTTL:MLLE:FVWIGYVSSGVNPLVYTLFNKTFR:AFGRYITCNY:A KSVKT:RK SS: YFRN
Human:    SCNQTTLQMLLEIFVWIGYVSSGVNPLVYTLFNKTFRDAFGRYITCNYRATKSVKTLRKRSSKIYFRNP
              *360      *370      *380      *390      *400      *410      *420
                                    TM7
```

Figure 2G

```
              *420         *430
     Dog:  RELKVFHETWNVKWY
Consensus:
   Human:  MAENSKFFKKHGIRNGINPAMYQSPMRLRSSTIQSSSIILLDTLLLTENEGDKTEEQVSYV
              *430         *440         *450         *460         *470         *480
```

Figure 7

```
            *1180      *1190      *1200      *1210      *1220      *1230      *1240      *1250
   Human: TTTGGCCGATATATCACCTGCAATTACCGGGCCACAAAGTCAGTAAAAACTCTCAGAAAAACGCTCCAGTAAGATCTACTT
Consensus: TTTGGCCGATATAT ACCTGCAATTACC GGCCA AA TCAGTAAAAACT TCAGAAAA GCTCCAG AA A CTACTT
  Canine: TTTGGCCGATATATTACCTGCAATTACCAGGCCATGAAATCAGTAAAATCAGTGTCCAGAAAATGTCCAGCAATAACTACTT
              ^1170      ^1180      ^1190      ^1200      ^1210    ^   1220      ^1230      ^1240

*1260      *1270      *1280      *1290      *1300      *1310      *1320      *1330
   Human: CCGGAATCCAATGGCAGAGAGAACTCTAAGTTTTTCAAGAAACATGAATTCGAAAATGGGATTAACCCTGCCATGTACCAGA
Consensus: CCG   AATGGCAGAGAGAACTC AAGTTTTTCA AGTTTCA GAAAC TGGAAT  GAAAATGG ATTAA CCTGCCA GTACCAGA
  Canine: CCGA----AATGGCAGAGAGAACTCAAAGTTTTTCAAAGTTTTTCATGAAACGTGGAATGTGAAATGGTATTAATCCTGCCAGTACCAGA
              ^1250      ^1260      ^1270      ^1280      ^1290      ^1300      ^1310      ^1320

*1340      *1350      *1360      *1370      *1380      *1390      *1400      *1410
   Human: GTCCAATGAGGCTCCGAAGTTCAACCATTCAGTCTTCATCAATCATTCTACTAGATACGCTTCTCCTCACTGAAAATGAA
Consensus: G CCAATGAGGCTC G AGTTCAACCATTCA  CTTC TCAATCATTCTACTAGATAC CTTC TC TCAC GAAAATGAA
  Canine: GCCCAATGAGGCTCTGCAGTTCAACCATTCAACCATTCACGCTTCCTCCTCAGCGCTTCCTCCTCAGCACTTCTCATCACAGAAAATGAA
              ^1330      ^1340      ^1350      ^1360      ^1370      ^1380      ^1390      ^1400

*1420      *1430      *1440
   Human: GGTGACAAAACTGAAGAGCAAGTTAGTTATGTATAG
Consensus: GGTGACAAAACTGAAGAGCAAGT AGTTATGTATAG
  Canine: GGTGACAAAACTGAAGAGCAAGTCAGTTATGTATAG
              ^1410      ^1420      ^1430
```

Figure 8

```
             *410      *420      *430      *440      *450      *460      *470      *480     Genbank No
     Human:  KRSSKIYFRNPMAENSKFFKKHGIRNGINPAMYQSPMRLRSSTIQSSSIILLDTLLLTENEGDKTEEQVSYV        AY136751
     Mouse:  KFSSTLCFGNSMVENSKFFTKHGIRNGINPAMYQSPMRLRSSTIQSSSIILLDT-LLTENDGDKAEEQVSYI        CAA78824
       Rat:  KCSSTLYFGNSMVENSKFFTKHGIRNGINPAMYQSPVRLRSSTIQSSSIILLNT-FLTENDGDKVEDQVSYI        NM_017250
      Frog:  NCSSRISFRNSMAENSKLIMKHGMKNGINPVMYQSPLRLCNAQLESSA-ILLDTLLLTENEAGKTEEQASYV        CAD71264
   Chicken:  KCSSRISFRNSVTENSKLFVMHGMRNGIPIMYQSPMRLRSSPIQASSAILLDTLLLTENEADKTEEQVSYV        NW06421
Puffer fish:  RMLTHISPRSSVAENAKLFTKQEIKN--ETTDYRSPLGCLQPSAQTSTGVVLDKILLTHTENCKQEERVSCV        CAC85912
 Zebra fish:  RR-SKISFRSSVTENSKRFMKHGMKNGISPVGYQSPIRHRSTQLQTSANIMLDTLLLTDNEDCKPDEHVSHV        BX57193
```

CANINE 5-HYDROXYTRYPTAMINE 2A AND 2B RECEPTOR

This application claims priority to U.S. Provisional Application No. 60/644,423, filed Jan. 14, 2005.

FIELD OF THE INVENTION

The present invention generally relates to canine 5-hydroxytryptamine 2A and 5-hydroxytryptamine 2B (5-HT2A and 5-HT2B, respectively) receptor materials, including polypeptides and polynucleotides encoding such polypeptides, and associated vectors and recombinant host cells. The invention also relates to methods of using such materials to assay compounds for their 5-HT2A and 5-HT2B modulating activity.

BACKGROUND OF THE INVENTION

The physiological actions of serotonin (5-hydroxytryptamine) are mediated by 14 different receptor subtypes, all but one belonging to the class of G-protein coupled receptors (Hoyer et al., 2002, *Pharmacol Biochem Behav,* 71:533-554). These receptors are divided into seven distinct classes ($5\text{-HT}_1$ to $5\text{-HT}_7$) largely on the basis of their structural and functional characteristics. The elucidation of the molecular, pharmacological, and physiological characterization of these receptors helps determine the roles of these receptors and their utilities as therapeutic targets.

The $5\text{-HT}_2$ receptor family comprises three receptor subtypes: $5\text{-HT}_{2A}$, $5\text{-HT}_{2B}$ and $5\text{-HT}_{2C}$ receptors (for a recent review, see Leysen et al., 2004, *Curr Drug Target CNS Neurol Disord,* 3:11-26). The $5\text{-HT}_2$ receptors are linked to the Gq family of G-proteins and subsequent activation of phospholipase C, induction of phosphoinositide metabolism and an increase in intracellular calcium concentration (Foguet, et al., 1992, *Embo J,* 11:3481-3487; Jerman et al., 2001, *Eur J Pharmacol,* 414:23-30; Porter, 1999, *Br J Pharmacol,* 128:13-20; Roth et al., 1998, *Pharmacology & Therapeutics* 79:231-257). Both $5\text{-HT}_{2A}$ and $5\text{-HT}_{2B}$ receptors are found in the central nervous system and periphery, whereas $5\text{-HT}_{2C}$ is restricted to the central nervous system (Hoyer et al., 2002, *Pharmacol Biochem Behav,* 71:533-554; Leysen, J. E., 2004, *Curr Drug Target CNS Neurol Disord* 3:11-26).

The $5\text{-HT}_{2A}$ receptors mediate contractile responses in vascular smooth muscle (Bhatnagar et al., 2004, *J Biol Chem,* 279 (33):34614-34623; Cohen et al., 1981, *J Pharmacol Exp Ther,* 218:421-425). In addition, platelet aggregation and increased capillary permeability following exposure to 5-HT have been attributed to $5\text{-HT}_{2A}$ receptor-mediated functions (Bhatnagar et al., 2004, *J Biol Chem,* 279 (33):34614-34623; de Chaffoy de Courcelles at al., 1985, *J Biol Chem* 260:7603-7608; Hall et al., 2000, *Synapse* 38:421-431). Centrally, $5\text{-HT}_{2A}$ receptors are principally located in cortex, claustrum, basal ganglia and in several brain stem nuclei (Fonseca et al., 2001, *Brain Res Mol Brain Res,* 89:11-19). $5\text{-HT}_{2A}$ receptors in the medial nucleus of the tractus solitarius play a role in 5-HT-induced hypotension and bradycardia (Huang et al., 2003, *J Comp Neurol,* 455:270-280). $5\text{-HT}_{2A}$ receptor activation also stimulates hormone secretion, e.g. ACTH, corticosterone, oxytocin, renin and prolactin secretion (Van de Kar et al., 2001, *J Neurosci,* 21:3572-3579). Moreover, $5\text{-HT}_{2A}$ receptor agonists mediate certain behavioral, emotional, and cognitive syndromes and disorders (Bhatnagar et al., 2004, *J Biol Chem,* 279 (33):34614-34623). Head twitching in rat and mice can be inhibited with selective $5\text{-HT}_{2A}$ antagonists (Schreiber et al., 1995, *J Pharmacol Exp Ther,* 273:101-112), and certain antipsychotics and antidepressant drugs are $5\text{-HT}_{2A}$ antagonists (Roth et al., 1998, *Pharmacology & Therapeutics* 79:231-257).

Activation of the $5\text{-HT}_{2B}$ receptor leads to fundic smooth muscle contraction (Foguet, et al., 1992, *Embo J,* 11:3481-3487; Kursar et al., 1992, *Mol Pharmacol* 42, 549-557). The $5\text{-HT}_{2B}$ receptor is found throughout the human gastrointestinal tract where it mediates contractile responses. The $5\text{-HT}_{2B}$ receptor has also been detected in discrete nuclei (Bonaventure et al., 2002, *Brain Res* 943:38-47; Duxon et al., 1997). Stimulation of $5\text{-HT}_{2B}$ receptors on endothelial cells of the cerebral arteries by 5-HT causes release of nitric oxide, leading to vascular relaxation (Schmuck et al., 1996, *Eur J Neurosci,* 8:959-967). Hence, stimulation of $5\text{-HT}_{2B}$ receptors on meningial blood vessels could be a trigger for migraine, perhaps explaining the reported prophylactic effect of $5\text{-HT}_2$ receptor antagonists (Schmuck et al., 1996, *Eur J Neurosci,* 8:959-967). $5\text{-HT}_{2B}$ receptor activation may also be involved in the development of cardiac valvulopathy associated with norfenfluramine and other serotonergic medication (Fitzgerald et al., 1999, *J Neurochem,* 72:2127-2134).

The $5\text{-HT}_{2A}$ and $5\text{-HT}_{2B}$ receptor subtypes have been cloned from several species. The $5\text{-HT}_{2A}$ receptors from hamster, human, monkey, mouse, pig, rat and sheep all have a similar length of 471 amino acids; the $5\text{-HT}_{2B}$ receptors from human, mouse and rat have a length of 481, 504 and 460 amino acids, respectively (for review, see Kroeze et al., 2002, *Curr Top Med Chem,* 2:507-528). Each of the genes for the $5\text{-HT}_{2A}$ and $5\text{-HT}_{2B}$ receptors possesses three exons. Species differences in the binding of certain ligands between human and rat $5\text{-HT}_{2A}$ receptors have been reported; for instance, ergolines appeared to display higher affinity for the rat than for the human receptor (Pazos et al., 1984, *Eur J Pharmacol,* 106:539-546). This is due to an amino acid variation ($S^{242}A$) in the fifth transmembrane domain between the human ($^{242}S$) and rat ($^{242}Ala$) $5\text{-HT}_{2A}$ receptor (Roth et al., 1998, *Pharmacology & Therapeutics,* 79:231-257). Additionally, differences in ligand binding between the human and rat $5\text{-HT}_{2B}$ receptors have been reported, with ergolines and certain atypical antipsychotics displaying higher affinity for the human $5\text{-HT}_{2B}$ receptor (Wainscott et al., 1996, *J Pharmacol Exp Ther,* 276:720-727).

The actions of 5-HT and 5-HT mimetics as they relate to many of the functions, syndromes, and disorders mentioned above have been studied in canine (e.g., see Bush, 1987, *J Pharmacol Exp Ther,* 240:674-682; Prins et al., 2001, *Br J Pharmacol,* 134:1351-1359; Shoji et al., 1990, *Eur J Pharmacol,* 190:247-250). The canine is also used to assess physiological liabilities, such as cardiovascular liabilities, of early drug candidates. There is a need to identify canine $5\text{-HT}_{2A}$ and $5\text{-HT}_{2B}$ receptors for use in interpreting data obtained from studies in canine, and in obtaining activity and binding affinity values for compounds in order to assay for ones that complex with or otherwise modulate canine $5\text{-HT}_{2A}$ or $5\text{-HT}_{2B}$ receptors.

SUMMARY OF THE INVENTION

The canine $5\text{-HT}_{2A}$ and $5\text{-HT}_{2B}$ receptor subtypes have now been identified and cloned, and their pharmacological characteristics have been compared to the human $5\text{-HT}_{2A}$ and $5\text{-HT}_{2B}$ receptor homologues.

In one general aspect, the invention is directed to isolated biologically active canine 5-hydroxytryptamine 2 receptor polypeptides having an amino acid sequence as set forth in SEQ ID NO.:8 or SEQ ID NO.:10 or functional variants thereof. Preferably, the polypeptides have an amino acid sequence as set forth in SEQ ID NO.:8 or SEQ ID NO.:10.

Another general aspect of the invention relates to isolated polynucleotides encoding the above-described 5-hydroxytryptamine 2 receptor polypeptides. Thus, the invention is directed to a polynucleotide encoding a canine 5-hydroxytryptamine 2 receptor polypeptide, where the polynucleotide has a sequence as set forth in SEQ ID NO.:7 or SEQ ID NO.:9 or a functional variant thereof. Preferably, the polynucleotide has a nucleic acid sequence as set forth in SEQ ID NO.:7 or SEQ ID NO.:9.

In other general aspects, the invention is directed to vectors each comprising one of the polynucleotides as described above operably linked to a promoter element that produces the 5-hydroxytryptamine 2 receptor RNA or expresses the canine 5-hydroxytryptamine 2 receptor polypeptide encoded by the polynucleotide in a transfected host cell.

In additional general aspects, the invention is directed to recombinant host cells transfected with one of the vectors as described above.

In further general aspects, the invention pertains to methods for identifying a compound that modulates an activity of a biologically active canine 5-hydroxytryptamine 2 receptor or a functional variant thereof. One such method comprises: (a) contacting a test sample comprising a compound with an assay reagent comprising the receptor and a 5-hydroxytryptamine 2 receptor ligand; (b) determining the biological activity of the receptor after performing step (a); and (c) comparing the biological activity determined in step (b) with a control measurement obtained by contacting a control sample not containing the compound with the assay reagent. Another such method comprises: (a) contacting a biologically active canine 5-hydroxytryptamine 2 receptor with a test compound and with a labeled ligand for the receptor; (b) determining the amount of the labeled ligand that complexes with the receptor; and (c) comparing the amount determined in step (b) with a control measurement obtained by contacting the receptor with the labeled ligand in the absence of the test compound. An additional method is a whole cell assay for detecting modulation of the canine 5-hydroxytryptamine 2 receptor by steps comprising: (a) contacting the compound and a cell that contains biologically active 5-hydroxytryptamine 2 receptor or a variant thereof; and (b) measuring for change in the cell in response to modified receptor function by the compound. In preferred embodiments of such methods, the 5-hydroxytryptamine 2 receptor material used in the assay is a component of a biological sample derived from a dog.

Other aspects and features of the invention will be apparent from the detailed description below with reference to the drawing figures.

BRIEF DESCRIPTION OF THE DRAWINGS

FIGS. 1A-1G provide an amino acid sequence comparison of human and dog 5-HT$_{2A}$ receptors. The consensus sequence is also shown. The putative seven transmembrane domains are indicated with solid lines.

FIGS. 2A-2G provide an amino acid sequence comparison of human and dog 5-HT$_{2B}$ receptors. The consensus sequence is also shown. The putative seven transmembrane domains are indicated with solid lines.

FIG. 3A shows a saturation binding isotherm of [$^3$H]5-HT binding to membranes isolated from COS-7 cells transfected with canine 5-HT$_{2A}$ receptor. FIG. 3B shows a saturation binding isotherm of [$^3$H]5-HT binding to membranes isolated from COS-7 cells transfected with canine 5-HT$_{2B}$ receptor. The non-specific binding was determined in the presence of 1 μM risperidone for both 5-HT$_{2A}$ and 5-HT$_{2B}$ receptors. Data points represent specific binding calculated by subtracting non-specific binding from total binding. Inset: Scatchard plot of the same data. The derived K$_D$ and B$_{max}$ values are listed in Table 1. Data are mean±S.E.M.

FIG. 4A shows a comparison of canine 5-HT$_{2A}$ and human 5-HT$_{2A}$ binding data. FIG. 4B shows a comparison of canine 5-HT$_{2B}$ and human 5-HT$_{2B}$ binding data. FIG. 4C shows a comparison of human 5-HT$_{2A}$ and human 5-HT$_{2B}$ binding data. FIG. 4D shows a comparison of canine 5-HT$_{2A}$ and canine 5-HT$_{2B}$ binding data. Correlation coefficient (r$^2$) and P values are given.

FIG. 7 provides a nucleotide sequence comparison between the human and canine 5-HT$_{2B}$ cDNA. The 5-nucleotide deletion in canine 5-HT$_{2B}$ cDNA is depicted with dashes. The numbers indicate the nucleotide position in cDNA starting with the translation starting codon (ATG). The putative translation stop codons for the human and canine 5-HT$_{2B}$ receptors are underlined.

FIG. 8 provides a C-terminal amino acid sequence comparison among human, mouse, rat, chicken, frog, puffer fish, and zebra fish 5-HT$_{2B}$ receptor proteins. The numbers indicate the amino acid position corresponding to the human 5-HT$_{2B}$ receptor.

DETAILED DESCRIPTION OF INVENTION AND ITS PREFERRED EMBODIMENTS

Figure 3A:
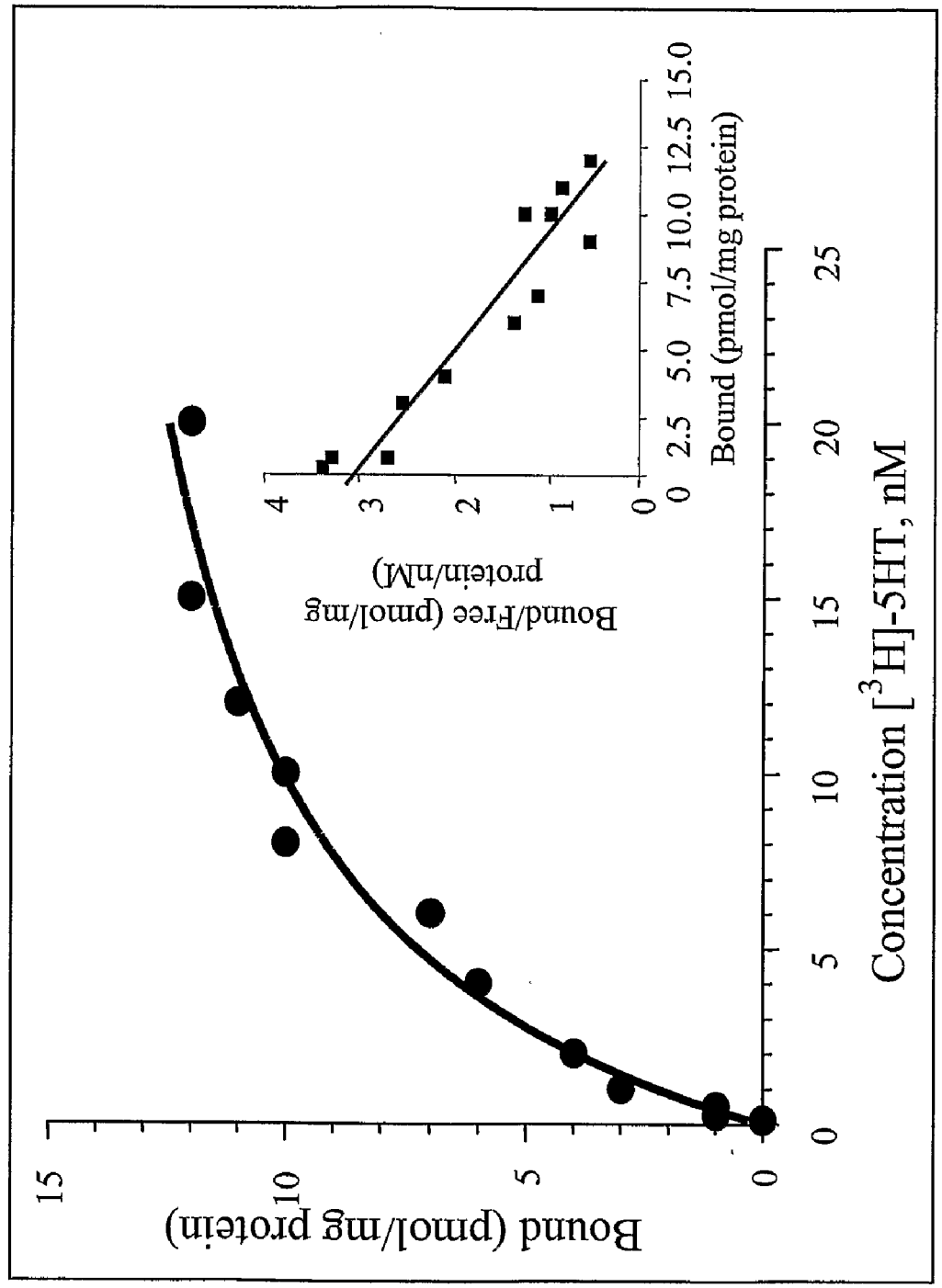
FIGS. 3A and 3B illustrate saturation binding isotherms of [$^3$H]5-HT binding to membranes expressing recombinant canine 5-HT$_{2A}$ and 5-HT$_{2A}$ receptors.

For the sake of brevity, the disclosures of all publications cited herein are incorporated by reference. Unless defined otherwise herein or as apparent from the context, all technical and scientific terms used herein have the same meaning as used in the art.

The following are abbreviations that are at times used in this specification: 5-HT=5-hydroxytryptamine; 5-HT$_2$=5-HT receptor subtype 2 member, e.g., 5-HT$_{2A}$ receptor or 5-HT$_{2B}$ receptor; 5-HT$_{2A}$=5-HT 2A receptor; 5-HT$_{2B}$=5-HT 2B receptor; bp=base pair; cpm=counts per minute; cAMP=cyclic adenosine monophosphate; cDNA=complementary DNA; ELISA=Enzyme-Linked Immunosorbent Assay; G protein=GTP-binding protein; GTP=guanosine 5'-triphosphate; FLIPR=fluorometric imaging plate reader; kb=kilobase (1000 base pairs); kDa=kilodalton; nt=nucleotide; PAGE=polyacrylamide gel electrophoresis; PCR=polymerase chain reaction.

The terms "including," "comprising" and "containing" are used herein in their open, non-limiting sense.

As summarized above, certain general aspects of the invention relate to isolated biologically active canine 5-hydroxytryptamine 2A and 5-hydroxytryptamine 2B receptor polypeptides, polynucleotides that encode them, expression vectors comprising such polynucleotides, and recombinant host cells transfected or transformed by such vectors.

"Polypeptide" refers to a peptidic molecule comprising two or more amino acids joined to each other in a chain by peptide bonds. As used herein, the term refers both to short chains, which are also referred to in the art as, e.g., peptides, oligopeptides and oligomers, and to longer chains, which are often referred to in the art as proteins, of which there are many types. The term refers to linear structures as well as semi-linear and non-linear structures, such as branched and circular structures.

A "biologically active" polypeptide or polynucleotide refers to a molecule that is active as determined in vivo or in vitro according to standard or conventional or accepted techniques. Such activities can be a direct activity, such as an association with or an enzymatic activity on a second protein, or an indirect activity, such as a cellular signaling activity mediated by interaction of the protein with a second protein. For example, an illustrative biological activity of a 5-$HT_2$ receptor ligand, such as 5-hydroxytryptamine, is its ability to bind or form a complex with either a 5-$HT_2$ receptor and initiate one or more signal transduction events conducted thereby. An exemplary biological activity of a canine 5-$HT_2$ receptor is that, upon binding to a ligand for the receptor, it activates a chain of events that alters the concentration of intracellular signaling molecules (second messenger molecules), such as cyclic AMP and calcium via activating G-protein, which has a high affinity to GTP. These intracellular signaling molecules in turn alter the physiology and behavior of the cell and animal. Such alterations in physiology can also be determined in vivo or in vitro according to known techniques, and can include, for example: alterations in hormone production, secretion, or activity, e.g., ACTH, corticosterone, oxytocin, renin, or prolactin production, secretion, or activity (Van de Kar et al., 2001, *J Neurosci,* 21(10):3572-3579; Saydoff et al., 1991, *J. Pharmacol. Exp. Ther.,* 257:95-99; Rittenhouse et al., 1994, *J. Pharmacol. Exp. Ther.,* 271:1647-1655; Rittenhouse et al., 1991, *J. Pharmacol. Exp. Ther.,* 259:58-65); alterations in smooth muscle contractility or relaxation, e.g., gastrointestinal tract contractility, vascular contractility or relaxation, and capillary permeability (Cohen et al., 1981, *J. Pharmacol. Exp. Ther.,* 218: 421-425; Adner et al., 2002, *Br. J. Pharmacol.,* 137(7):971-982; 2004; Owaga et al., 2004, *Vascul. Pharmacol.,* 41(1):7-13; Boehme et al., 2004, *J Immunol,* 2004, 173(6):3599-3603; Schmuck et al., 1996, *Eur. J. Neurosci.,* 8:959-967; de Chaffoy de Courcelles et al., 1985, J. Biol. Chem., 260:7603-7608; Cazzola et al., 1992, *Immunopharmacology,* 23:21-28; and Fitzgerald et al., 1999, *J. Neurochem.,* 72:2127-2134; alterations in platelet aggregation (de Chaffoy de Courcelles et al., 1985, J. Biol. Chem., 260:7603-7608); or alterations in mental, emotional, or behavioral status (Kantor et al., *Br. J. Pharmacol.,* 2004, 142(8):1332-1342; Massou et al., 1997, *Psychopharmacology* (Berl), 133:99-101; Aubert et al., 2000, *Int. J. Obes. Relat. Metab. Disord.,* 24:920-924; Du, 2000, *Am. J. Med. Genet.,* 96:56-60; Meltzer, 1999, *Neuropsychopharmacology,* 21:106 S-115S; Meyer et al., 1999, *Psychopharmacology* (Berl), 144:279-281; Roth et al., 1998, *Pharmacology and Therapeutics,* 79:231-257; Schreiber et al., 1995, *J. Pharmacol. Exp. Ther.,* 273:101-112; Schechter et al., 1988, *Psychopharmacology* (Berl) 94:342-346; Sorensen et al., 1993, *J. Pharmacol. Exp. Ther.,* 266:684-691).

A "functional variant" of a polypeptide refers to a post-translationally modified form, homolog, or variant of a designated polypeptide having essentially the same biological activity as the designated one. With respect to the canine 5-$HT_2$ receptor polypeptides described herein, functional variants may be routinely determined by making one or more post-translational modifications to a polypeptide and testing the biological activity of the resulting variant. See, e.g., Wold, "Posttranslational Protein Modifications: Perspectives and Prospects," pp. 1-12 in POSTTRANSLATIONAL COVALENT MODIFICATION OF PROTEINS, Johnson (ed.), Academic Press, New York (1983). For instance, polypeptides can be post-translationally modified, including via natural processing or through human manipulation, which may result in variants that are not entirely linear. To further illustrate, during post-translational modification of the peptide a methionine residue at the $NH_2$-terminus may be deleted. Accordingly, the methionine-containing and the methionine-less amino terminal variants of a protein may be prepared.

An "isolated" polypeptide is a polypeptide substantially free of or separated from cellular material or other contaminating proteins when the polypeptide is obtained from the cell or tissue source from which the polypeptide is produced, or substantially free of chemical precursors or other chemicals when the polypeptide is chemically synthesized (e.g., purified). For example, protein that is substantially free of cellular material may include preparations of protein having less than about 30%, or preferably 20%, or more preferably 10%, or even more preferably 5%, or yet more preferably 1% (by dry weight), of contaminating proteins.

In preferred embodiments, the isolated polypeptide is substantially pure. Thus, when the protein or biologically active portion thereof is recombinantly produced, it is substantially free of culture medium, e.g., culture medium representing less than about 20%, or more preferably 10%, or even more preferably 5%, or yet more preferably 1%, of the volume of the protein preparation. When the protein is produced by chemical synthesis, it is substantially free of chemical precursors or other chemicals, i.e., it is separated from chemical precursors or other chemicals that are involved in the synthesis of the protein. Accordingly such preparations of the polypeptide have less than about 30%, or preferably 20%, or more preferably 10%, or even more preferably 5%, or yet more preferably 1% (by dry weight), of chemical precursors or compounds other than the polypeptide of interest.

Isolated polypeptides can have several different physical forms. The isolated polypeptide can exist as a full-length nascent or unprocessed polypeptide, or as partially processed polypeptides or combinations of processed polypeptides. The full-length nascent polypeptide can be post-translationally modified by specific proteolytic cleavage events that result in the formation of fragments of the full-length nascent polypeptide. A fragment, or physical association of fragments, can have the biological activity associated with the full-length polypeptide; of course, the degree of biological activity associated with individual fragments can vary.

Polypeptides of the invention may be prepared using polynucleotides of the invention. The term "polynucleotide" as used herein refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single- or double-stranded. However, linkages may include any of the linkages known in the art, including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like.

An "isolated" polynucleotide is one that is substantially separated from or free of nucleic acid molecules with differing nucleic acid sequences. Embodiments of the isolated polynucleotide molecule of the invention include cDNA, genomic DNA and RNA and antisense RNA. Preferred polynucleotides are obtained from biological samples obtained from a dog, such as from blood samples or tissue specimens.

The invention also embraces polymorphisms of a specified polynucleotide and polypeptides encoded thereby. "Polymorphism" refers to a set of genetic variants at a particular genetic locus among individuals in a population.

Canine 5-HT$_2$ receptor polynucleotides may be inserted into expression vectors for introduction of such polynucleotides into host cells for the expression, i.e., production of the encoded mRNA or protein, of the canine 5-HT$_2$ receptor polypeptides encoded by such polynucleotides in such host cells. The expressed canine 5-HT$_2$ receptor polypeptides from the resulting recombinant host cells are isolated for various uses in vitro, or serve to modulate various other in vivo activities within such recombinant host cells.

The term "vector" refers to a nucleic acid molecule capable of transporting another nucleic acid to which it has been linked. One type of vector is a plasmid, which refers to a circular double-stranded DNA loop into which additional DNA segments can be inserted. Another type of vector is a viral vector wherein additional DNA segments can be inserted. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors—expression vectors—are capable of directing the expression of genes to which they are operably linked. Vectors of utility in recombinant DNA techniques may be in the form of plasmids. Alternatively, other forms of vectors, such as viral vectors (e.g., replication defective retroviruses, adenoviruses and adeno-associated viruses), which serve equivalent functions, may be used.

A "host cell" refers to a cell that contains a DNA molecule either on a vector or integrated into a cell chromosome. A host cell can be either a native host cell that contains the DNA molecule endogenously or a recombinant host cell.

One example of a host cell is a recombinant host cell, which is a cell that has been transformed or transfected by an exogenous DNA sequence. A cell has been transformed by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA. A "clone" is a population of cells derived from a single cell or common ancestor by mitosis. A "cell line" is a clone of a primary cell that is capable of stable growth in vitro for many generations.

Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila* and silkworm derived cell lines. A recombinant host cell refers not only to the particular subject cell, but also to the progeny or potential progeny of such a cell. Because certain modifications can occur in succeeding generations due to either mutation or environmental influences, such progeny may not be identical to the parent cell, but are still intended to be included within the scope of the term.

Vectors of the present invention also include specifically designed expression systems that allow the shuttling of DNA between hosts, such as bacteria-yeast or bacteria-animal cells or bacteria-fungal cells or bacteria-invertebrate cells. Numerous cloning vectors are known in the art and the selection of an appropriate cloning vector is within the purview of the artisan. For other suitable expression systems for both prokaryotic and eukaryotic cells, see e.g., chapters 16 and 17 of Maniatis et al., Molecular Cloning: A Laboratory Manual, Second Edition (Cold Spring Harbor Laboratory, Cold Spring Harbor, N.Y., 1989).

To obtain high level expression of a cloned gene or nucleic acid, such as a cDNA encoding a canine 5-HT$_2$ receptor polypeptide, a canine 5-HT$_2$ receptor sequence is preferably subcloned into an expression vector that contains a strong promoter to direct transcription, a transcription/translation terminator, and, if for a nucleic acid encoding a protein, a ribosome binding site for translational initiation. Suitable bacterial promoters are known in the art and are described, e.g., by Sambrook et al., Molecular Cloning: A Laboratory Manual, Third Edition, Cold Spring Harbor Laboratory, Cold Spring Harbor, N.Y., 2001, and "Current Protocols in Molecular Biology", Ausubel et al. (eds.), Greene Publishing Association and John Wiley Interscience, New York, 1992. Bacterial expression systems for expressing the CCK1 proteins disclosed in the present invention are available in, e.g., *E. coli, Bacillus* sp., and *Salmonella* (Palva et al., 1983, *Gene*, 22:229-235; Mosbach et al., 1983, *Nature*, 302:543-545). Kits for such expression systems are commercially available. Eukaryotic expression systems for mammalian cells, yeast, and insect cells are known in the art and are also commercially available. In exemplary embodiments, the eukaryotic expression vector is an adenoviral vector, an adeno-associated vector, or a retroviral vector.

A "promoter" is a regulatory sequence of DNA that is involved in the binding of RNA polymerase to initiate transcription of a gene. Promoters are often upstream (i.e., 5' to) the transcription initiation site of the gene. A "gene" is a segment of DNA involved in producing a peptide, polypeptide, or protein, including the coding region, non-coding regions preceding (5'UTR) and following (3'UTR) coding region, as well as intervening non-coding sequences (introns) between individual coding segments (exons). "Coding" refers to the specification of particular amino acids or termination signals in three-base triplets (codons) of DNA or mRNA.

The promoter used to direct expression of a heterologous canine 5-HT$_2$ receptor-encoding polynucleotide may be routinely selected to suit the particular application. The promoter is optionally positioned about the same distance from the heterologous transcription start site as it is from the transcription start site in its natural setting. As will be apparent to the artisan, however, some variation in this distance can be accommodated without loss of promoter function.

In addition to the promoter, the expression vector may contain a transcription unit or expression cassette that contains all the additional elements required for the expression of the canine 5-$HT_2$ receptor-encoding polynucleotide in host cells. An exemplary expression cassette contains a promoter operably linked to the polynucleotide sequence encoding a canine 5-$HT_2$ receptor polypeptide, and signals required for efficient polyadenylation of the transcript, ribosome binding sites, and translation termination. The polynucleotide sequence encoding a canine 5-$HT_2$ receptor polypeptide may be linked to a cleavable signal peptide sequence to promote secretion of the encoded protein by the transfected cell. Exemplary signal peptides include the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes.

In exemplary embodiments, any of the vectors suitable for expression in eukaryotic or prokaryotic cells known in the art may be used. Exemplary bacterial expression vectors include plasmids such as pBR322-based plasmids, pSKF, pET23D, and fusion expression systems such as GST and LacZ. Examples of mammalian expression vectors include, e.g., pCDM8 (Seed, 1987, *Nature,* 329:840) and pMT2PC (Kaufinan et al., 1987, *EMBO J,* 6:187-195). Commercially available mammalian expression vectors which can be suitable for recombinant 5-$HT_2$ expression include, for example, pMAM-neo (Clontech), pcDNA3 (Invitrogen), pCiNeo (Promega), pMC1neo (Stratagene), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRS-Vgpt (ATCC 37199), pRSVneo (ATCC 37198), pSV2-dhfr (ATCC 37146), pUCTag (ATCC 37460), and 1ZD35 (ATCC 37565).

In yet other exemplary embodiments, the recombinant mammalian expression vector is capable of directing expression of the nucleic acid preferentially in a particular cell type (e.g., tissue-specific regulatory elements are used to express the nucleic acid). Various tissue-specific regulatory elements are known in the art. Examples of suitable tissue-specific promoters include the albumin promoter (liver-specific; Pinkert et al., 1987, *Genes Dev.,* 1:268-277), lymphoid-specific promoters (Calame et al., 1988, *Adv. Immunol.,* 43:235-275), such as promoters of T cell receptors (Winoto et al., 1989, *EMBO J,* 8:729-733), and immunoglobulins (Baneji et al., 1983, *Cell,* 33:729-740; Queen et al., 1983, *Cell,* 33:741-748), neuron-specific promoters (e.g., the neurofilament promoter; Byme et al., 1989, *Proc. Natl. Acad. Sci. USA,* 86:5473-5477), pancreas-specific promoters (Edlund et al., 1985, *Science,* 230:912-916), and mammary gland-specific promoters (e.g., milk whey promoter; U.S. Pat. No. 4,873,316 and European Patent Publication No. 264,166). Developmentally regulated promoters also include, for example, the marine hox promoters (Kessel et al., 1990, *Science,* 249:374-379) and the beta-fetoprotein promoter (Campes et al., 1989, *Genes Dev.,* 3:537-546).

Epitope tags can also be added to recombinant proteins to provide convenient methods of isolation, e.g., c-myc, hemoglutinin (HA)-tag, 6-His tag, maltose binding protein, VSV-G tag, or anti-FLAG tag, and others known in the art.

Expression vectors containing regulatory elements from eukaryotic viruses can be used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAM-neo 5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

In exemplary embodiments, the pCiNeo expression vector is employed to introduce the canine 5-$HT_2$ receptor polynucleotides of the present invention into host cells and to express them in transformed or transfected cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding a canine 5-$HT_2$ receptor polypeptide under the direction of the polyhedrin promoter or other strong baculovirus promoters.

The elements that can be included in expression vectors also include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene may be selected from the many resistance genes known in the art. The prokaryotic sequences may be chosen such that they do not interfere with the replication of the DNA in eukaryotic cells, if necessary or desired.

Known transfection methods may be used to produce bacterial, mammalian, yeast or insect cell lines that express large quantities of a canine 5-$HT_2$ receptor polypeptide, which are then purified using standard techniques (see, e.g., Colley et al., 1989, *J. Biol. Chem.* 264:17619-17622); "Guide to Protein Purification," in *Methods in Enzymology,* vol. 182 (Deutscher, ed., 1990)). Transformation of eukaryotic and prokaryotic cells may be performed according to standard techniques (see, e.g., Morrison, *J. Bact,* 1977, 132:349-351; Clark-Curtiss & Curtiss, *Methods in Enzymology* 101:347-362 (Wu et al., eds, 1983)).

Any of the known procedures suitable for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the Gene Gun), or any other known methods for introducing cloned genomic DNA, cDNA, synthetic DNA or other foreign genetic material into a host cell (see, e.g., Sambrook et al., supra). The selected genetic engineering procedure should be capable of successfully introducing at least one gene into the host cell capable of expressing a canine 5-$HT_2$ receptor RNA, mRNA, cDNA, or gene.

For stable transfection of mammalian cells, it will be apparent that, depending upon the expression vector and transfection technique used, only a small fraction of cells may integrate the foreign DNA into their genome. In order to identify and select these integrants, a gene that encodes a selectable marker (e.g., for resistance to antibiotics) may be introduced into the host cells along with the gene of interest. Exemplary selectable markers include those that confer resistance to drugs, such as G418, puromycin, Geneticin, hygromycin and methotrexate. Cells stably transfected with the introduced nucleic acid can be identified by drug selection (e.g., cells that have incorporated the selectable marker gene will survive, while the other cells will die).

A heterologous regulatory element can be inserted into a stable cell line or cloned microorganism, such that it is operatively linked with and activates expression of endogenous genes, using techniques such as targeted homologous recombination, e.g., as described in U.S. Pat. No. 5,272,071 and WIPO Publication No. WO 91/06667.

After the expression vector is introduced into the cells, the transfected cells are cultured under conditions favoring expression of the canine 5-$HT_2$ receptor polypeptide, which is recovered from the culture using standard techniques identified below. Methods of culturing prokaryotic or eukaryotic cells are known and are taught, e.g., in Ausubel et al., Sambrook et al., and in Freshney, CULTURE OF ANIMAL CELLS, 3d ed., (1993), Wiley-Liss.

The isolated polypeptides of the present invention may be prepared by a variety of techniques. For example, canine 5-$HT_2$ receptor polypeptides may be isolated from canine tissue such as brain, spleen, placenta, lung, liver, kidney, pancreas, prostate, testis, ovary, small intestine, colon, lymph node, and tonsils, or any other natural source of canine 5-$HT_2$ receptor polypeptides. Bodily fluids such as blood, blood plasma, serum, seminal fluid, urine, or any other mammalian bodily fluid can also serve as sources of natural canine 5-$HT_2$ receptor polypeptides. Cultured mammalian cell lines are still further exemplary sources of natural canine 5-$HT_2$ receptor polypeptides.

Alternatively, recombinant canine 5-$HT_2$ polypeptides may be produced from any suitable bacterial or eukaryotic expression system, such as those described above. Such canine 5-$HT_2$ proteins may be isolated by standard purification techniques, including selective precipitation with such substances as ammonium sulfate; column chromatography; and immunopurification methods (see, e.g., Scopes, PROTEIN PURIFICATION: PRINCIPLES AND PRACTICE (1982); U.S. Pat. No. 4,673,641; Ausubel et al., supra; and Sambrook et al., supra).

A number of procedures may be employed when recombinant canine 5-$HT_2$ receptor polypeptides are being purified. For example, proteins having established molecular adhesion properties can be reversibly fused to the canine 5-$HT_2$ receptor polypeptide. With the appropriate ligand, a canine 5-$HT_2$ receptor polypeptide may be selectively adsorbed to a purification column and then freed from the column in a substantially pure form, and the fused protein removed by enzymatic activity. Canine 5-$HT_2$ receptor proteins may also be purified using immunoaffinity columns.

Recombinant proteins may be expressed by transformed bacteria or eukaryotic cells in large amounts, preferably after promoter induction, but expression can be constitutive. Promoter induction with IPTG is one example of an inducible promoter system. Cells may be grown according to standard procedures in the art. Fresh or frozen cells may be used for isolation of protein.

Proteins expressed in bacteria may form insoluble aggregates (inclusion bodies). Several known protocols are suitable for isolation of canine 5-$HT_2$ receptor inclusion bodies. For example, isolation may involve the extraction, separation and/or purification of inclusion bodies by disruption of bacterial cells, e.g., by incubation in a buffer of 50 mM TRIS/HCl pH 7.5, 50 mM NaCl, 5 mM $MgCl_2$, 1 mM DTT, 0.1 mM ATP, and 1 mM PMSF. The cell suspension can be lysed using 2-3 passages through a French press, homogenized using a Polytron (Brinkman Instruments) or sonicated on ice. Alternate methods of lysing bacteria will be apparent to those of ordinary skill in the art (see, e.g., Sambrook et al., supra; Ausubel et al., supra).

If necessary or desired, the inclusion bodies may be solubilized, and the lysed cell suspension centrifuged to remove unwanted insoluble matter. Proteins that formed the inclusion bodies may be renatured by dilution or dialysis with a compatible buffer. Suitable solvents include urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, may be undesirable for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of biologically active protein. Other suitable buffers are known in the art. Canine 5-$HT_2$ receptor polypeptides may be separated from other bacterial proteins by standard separation techniques, e.g., with Ni-NTA agarose resin.

Alternatively, 5-$HT_2$ receptor polypeptides may be purified from bacteria periplasm. After lysis of the bacteria, when a canine 5-$HT_2$ receptor protein is exported into the periplasm of the bacteria, the periplasmic fraction of the bacteria can be isolated by cold osmotic shock or another method known in the art. To isolate recombinant proteins from the periplasm, the bacterial cells may be centrifuged to form a pellet. The pellet may be resuspended in a buffer containing 20% sucrose. To lyse the cells, the bacteria may be centrifuged and the pellet resuspended in ice-cold 5 mM $MgSO_4$ and kept in an ice bath for approximately 10 minutes. The cell suspension may be centrifuged and the supernatant decanted and saved. The recombinant proteins present in the supernatant can be separated from the host proteins by standard separation techniques known in the art.

As an initial step, e.g., if a protein mixture is complex, an initial salt fractionation can be used to separate many of the unwanted host cell proteins (or proteins derived from the cell culture media) from the recombinant protein of interest. An exemplary salt is ammonium sulfate, which precipitates proteins by effectively reducing the amount of water in the protein mixture. Proteins then precipitate on the basis of their solubility. The more hydrophobic a protein is, the more likely it is to precipitate at lower ammonium sulfate concentrations. An exemplary isolation protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration sufficient to precipitate the protein of interest. The precipitate is then solubilized in buffer and the excess salt removed to achieve the desired purity, e.g., through dialysis or diafiltration. Other known methods that rely on solubility of proteins, such as cold ethanol precipitation, can be used to fractionate complex protein mixtures.

In other examples, the molecular weight of a canine 5-$HT_2$ receptor can be used to isolate it from proteins of greater and lesser size using ultrafiltration through membranes of different pore size (for example, Amicon or Millipore membranes). In an illustrative technique, the protein mixture is first ultrafiltered through a membrane with a pore size that has a lower molecular weight cut-off than the molecular weight of the protein of interest. The retentate of the ultrafiltration is then ultrafiltered against a membrane with a molecular cut-off greater than the molecular weight of the protein of interest. The recombinant protein will pass through the membrane into the filtrate. The filtrate can then be chromatographed.

Canine 5-$HT_2$ receptor proteins can also be separated from other proteins on the basis of net surface charge, hydrophobicity, and affinity for heterologous molecules. In addition, antibodies raised against proteins can be conjugated to column matrices and the proteins immunopurified. It will be apparent to those of ordinary skill in the art that chromatographic techniques can be performed at any suitable scale and using equipment from many different manufacturers (e.g., Pharmacia Biotech).

Another general aspect of the invention relates to a method of identifying compounds that modulate a biological activity of a 5-$HT_2$ receptor in test biological samples. Such assay methods are therefore useful for screening compounds for modulation of 5-$HT_{2A}$ or 5-$HT_{2B}$ receptor activity.

"Modulators" include both inhibitors and activators. Inhibitors decrease, prevent, inactivate, desensitize or down-regulate a canine 5-$HT_2$ receptor expression or activity. Activators increase, activate, facilitate, sensitize or up-regulate complex expression or activity.

Modulators of 5-$HT_{2A}$ or 5-$HT_{2B}$ receptor activity may be useful in treating subjects suffering from a disease, disorder, condition, or syndrome, mediated by aberrant 5-$HT_{2A}$ or 5-$HT_{2B}$ receptor activity, such as the following: behavioral, emotional, and cognitive syndromes and disorders, such as psychoses, depression, schizophrenia, bipolar disorder, aggressive behavior, impaired affect, sleep-wake cycle disorders, and eating disorders (see, e.g., Kantor et al., Br. J. Pharmacol., 2004, 142(8):1332-1342; Massou et al., 1997, Psychopharmacology (Berl), 133:99-101; Aubert et al., 2000, Int. J. Obes. Relat. Metab. Disord., 24:920-924; Du, 2000, Am. J. Med. Genet., 96:56-60; Meltzer, 1999, Neuropsychopharmacology, 21:106 S-115S; Meyer et al., 1999, Psychopharmacology (Berl), 144:279-281; Roth et al., 1998, Pharmacology and Therapeutics, 79:231-257; Schreiber et al., 1995, J. Pharmacol. Exp. Ther., 273:101-112; Schechter et al., 1988, Psychopharmacology (Berl) 94:342-346; and Sorensen et al., 1993, J. Pharmacol. Exp. Ther., 266:684-691); diseases, disorders, conditions, or syndromes associated with abnormal hormone production, secretion, or activity, e.g., abnormal ACTH, corticosterone, oxytocin, renin, and prolactin production, secretion, or activity, such as hypercortisolemia, hypocortisolemia, Cushing's syndrome, Addison's disease, congestive heart failure, renal failure, type 2 diabetes mellitus, lupus erythematosus, hypoprolacitnemia, hyperprolactinemia, and infertility (see, e.g., Van de Kar et al., 2001, J Neurosci, 21(10):3572-3579; Saydoff et al., 1991, J. Pharmacol. Exp. Ther., 257:95-99; Rittenhouse et al., 1994, J. Pharmacol. Exp. Ther., 271:1647-1655; Rittenhouse et al., 1991, J. Pharmacol. Exp. Ther., 259:58-651; Baluta et al., 2004, Rom. J. Intern. Med., 42(2):277-288; Jara et al., 2004, Lupus, 10(10):748-756; Gonzales et al., 1989, Arch. Androl., 23(3):259-265; and Ufearo et al., 1995, Clin. Pharmacol. Ther. 58(3):354-359); diseases, disorders, conditions or syndromes associated with abnormal smooth muscle contractility or relaxation, e.g., abnormal vascular contractility or relaxation, abnormal gastrointestinal tract contractility, abnormal capillary permeability, such as peripheral vascular disease, hypotension, hypertension, bronchoconstriction, chronic airway obstruction, asthma, and migraine; and diseases, disorders, conditions or syndromes associated with abnormal cardiovascular function, such as bradycardia and cardiac valvulopathy, myocardial infarction, and congestive heart failure (see, e.g., Cohen et al., 1981, J. Pharmacol. Exp. Ther., 218:421-425; Adner et al., 2002, Br. J. Pharmacol., 137(7):971-982; 2004; Owaga et al., 2004, Vascul. Pharmacol., 41(1):7-13; Boehme et al., 2004, J Immunol, 2004, 173 (6):3599-3603; Schmuck et al., 1996, Eur. J. Neurosci., 8:959-967; de Chaffoy de Courcelles et al., 1985, J. Biol. Chem., 260:7603-7608; Cazzola et al., 1992, Immunopharmacology, 23:21-28; Fitzgerald et al., 1999, J. Neurochem., 72:2127-2134; Schmidt et al., 2004, Am. J. Cardiovasc. Drugs, 4(6):361-368; and Sethi et al., 2004, Mol. Cell. Biochem., 263(1-2):11-20). In a preferred embodiment, the 5-$HT_2$ receptor activity is a 5-$HT_{2A}$ receptor activity. In another preferred embodiment, the 5-$HT_2$ receptor activity is a 5-$HT_{2B}$ receptor activity.

"Modulators" include both inhibitors and activators. "Inhibitors" refer to compounds that decrease, prevent, inactivate, desensitize or down-regulate a canine 5-$HT_2$ receptor expression or activity. "Activators" refer to compounds that increase, activate, facilitate, sensitize or up-regulate a canine 5-$HT_2$ receptor expression or activity.

The compound assay or screening methods can be performed using laboratory formats or in assays adapted for high throughput. High-throughput assays or screens (HTS) allow easy screening of multiple samples simultaneously or single samples rapidly, and can include the capacity for robotic manipulation. High-throughput assays may be designed or optimized to reduce reagent usage or minimize the number of manipulations in order to achieve the analysis desired. Examples of assay formats include 96-well or 384-well plates, levitating droplets, microassays and lab-on-a-chip formats or microchannel chips used for liquid-handling experiments. Of course, as miniaturization of plastic molds and liquid-handling devices are advanced, or as improved assay devices are designed, greater numbers of compounds may be screened more efficiently using an assay in accordance with the invention.

Candidate compounds for screening can be selected from numerous chemical classes, preferably from classes of organic compounds. Although candidate compounds can be macromolecules, preferably the candidate compounds are small-molecule organic compounds, i.e., those having a molecular weight of greater from 50 to 2500. Candidate compounds may be selected to possess one or more functional chemical groups suspected to have structural interaction with polypeptides. Exemplary candidate compounds have at least an amine, carbonyl, hydroxyl or carboxyl group, preferably at least two such functional groups, and more preferably at least three such functional groups. The candidate compounds can comprise cyclic carbon or heterocyclic structural moieties and/or aromatic or polyaromatic structural moieties substituted with one or more of the above-exemplified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound may be a DNA or RNA molecule, although modified nucleic acids having non-natural bonds or subunits are also contemplated.

Candidate compounds may be obtained from a variety of sources, including libraries of synthetic or natural compounds. For example, numerous means are available for random or directed synthesis of a variety of organic compounds and biomolecules, including expression of randomized oligonucleotides, synthetic organic combinatorial libraries, phage display libraries of random peptides, and the like.

Candidate compounds can also be obtained using any of the numerous approaches in combinatorial library methods known in the art, including: biological libraries; spatially addressable parallel solid-phase or solution-phase libraries; synthetic library methods requiring deconvolution; a one-bead-one-compound library method; and synthetic library methods using affinity chromatography selection (see, e.g., Lam, 1997, *Anti-Cancer Drug Des.* 12:145). Alternatively, libraries of natural compounds in the form of bacterial, fungal, plant and animal extracts are available or may be routinely produced. Additionally, natural and synthetically produced libraries and compounds can be routinely modified through conventional chemical, physical, and biochemical means.

Furthermore, known pharmacological agents can be subjected to directed or random chemical modifications, such as acylation, alkylation, esterification, and amidification, to produce structural analogs of the agents. Candidate compounds may be selected randomly or can be based on existing compounds that bind to and/or modulate the function or activity of a human 5-HT$_2$ receptor family member. Therefore, a source of candidate agents is known or screened libraries of molecules including activators or inhibitors of human 5-HT$_2$ receptors. The structures of such compounds may be changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions.

A variety of other reagents also can be included in the assay mixture. These include reagents such as salts, buffers, neutral proteins (e.g., albumin), and detergents that can be used to facilitate optimal protein-protein and/or protein-nucleic acid binding. Such a reagent can also reduce non-specific or background interactions of the reaction components. Other reagents that improve the efficiency of the assay, such as nuclease inhibitors, antimicrobial agents, and the like, can also be used.

Examples of methods for the synthesis of molecular libraries can be found in the art, for example in Zuckermann et al., 1994, *J. Med. Chem.*, 37:2678-2685. Libraries of compounds can be presented in solution (e.g., Houghten (1992), *Biotechniques*, 13:412-421), or on beads (Lam 1991, *Nature*, 354:82-84), chips (Fodor 1993, *Nature*, 364:555-556), bacteria (U.S. Pat. No. 5,223,409), spores (U.S. Pat. No. 5,571,698), plasmids (Cull et al. 1992, *Proc. Natl. Acad. Sci. USA*, 9:1865-1869) or phage (see e.g., Scott and Smith 1990, *Science*, 249:386-390).

In one illustrative embodiment, the inventive assay provides a whole cell method to detect compound modulation of a canine 5-HT$_2$ receptor, comprising: (a) contacting a compound and a cell that contains biologically active canine 5-HT$_2$ receptor material; and (b) measuring a change in the cell in response to modified receptor function by the compound. The amount of time for cellular contact with the compound may be empirically determined, for example, by running a time course with a reference 5-HT$_2$ receptor modulator and measuring cellular changes as a function of time. In a preferred embodiment, the canine 5-HT$_2$ receptor material is canine 5-HT$_{2A}$ receptor material. In another preferred embodiment, the canine 5-HT$_2$ receptor material is canine 5-HT$_{2B}$ receptor material.

The measurement may be conducted by comparing a cell that has been exposed to a compound to an identical cell that has not been similarly exposed to the compound or, alternatively, to a cell that has been exposed to a reference compound (e.g., a known 5-HT$_2$ modulator). Alternatively two cells, one containing the biologically active 5-HT$_2$ receptor and a second cell identical to the first but lacking such receptor could be both be contacted with the same compound and compared for differences between the two cells. This technique is also useful in establishing the background noise of these assays. Artisans will appreciate that these control mechanisms also allow easy selection of cellular changes that are responsive to modulation of the receptor.

The cellular changes suitable for the method of the present invention comprise directly measuring changes in the activity, function or quantity of canine 5-HT$_2$ receptor protein, or by measuring downstream effects of the receptor function, for example by measuring secondary messenger concentrations or changes in transcription or by changes in protein levels of genes that are transcriptionally influenced by the receptor, or by measuring phenotypic changes in the cell. Preferred measurement means include measurement of changes in the quantity of canine 5-HT$_2$ protein, changes in the functional activity of the receptor, changes in the quantity of mRNA, changes in intracellular protein, changes in cell surface protein or secreted protein, or changes in Ca$^{2+}$, cAMP or GTP concentration. Changes in the levels of mRNA may be detected by reverse transcription polymerase chain reaction (RT-PCR) or by differential gene expression. Immunoaffinity, ligand affinity, or enzymatic measurement quantitates 5-HT$_2$ modulator-induced changes in levels of specific proteins in host cells. Where the protein is an enzyme, the induction of protein may be monitored by cleavage of a fluorogenic or colorimetric substrate.

Preferred detection means for cell surface protein include flow cytometry or statistical cell imaging. In both techniques the protein of interest is localized at the cell surface, labeled with a specific fluorescent probe, and detected via the degree of cellular fluorescence. In flow cytometry, the cells are analyzed in a solution, whereas in cellular imaging techniques, a field of cells is compared for relative fluorescence.

The present invention is also directed to methods for screening for compounds that modulate the expression of DNA or RNA encoding a canine 5-HT$_2$ receptor as well as the function of the receptor protein in vivo. Compounds may modulate by increasing or attenuating the expression of DNA or RNA encoding the receptor, or the function of the receptor protein. Compounds that modulate the expression of DNA or RNA encoding the receptor or the function of the receptor protein may be detected by a variety of assays. The assay may be a simple "yes/no" assay to determine whether there is a change in expression or function. The assay may be made quantitatively by comparing the expression or function of a test sample with the levels of expression or function in a standard sample.

In another embodiment, the invention relates to a method of identifying a compound that increases or decreases a biological activity of a canine 5-HT$_2$ receptor, comprising the steps of: (a) contacting (i) a test sample comprising a compound with (ii) an assay reagent comprising a biologically active canine 5-HT$_2$ receptor polypeptide or a functional variant thereof and a 5-HT$_2$ receptor ligand; (b) determining the biological activity of the receptor after performing step (a); and (c) comparing the biological activity determined in step (b) with a control measurement obtained by contacting a control sample not containing the compound with the assay reagent. In a preferred embodiment, the canine 5-HT$_2$ receptor is a 5-HT$_{2A}$ receptor. In another preferred embodiment, the canine 5-HT$_2$ receptor is a 5-HT$_{2B}$ receptor.

A "ligand" or a "ligand component" refers to a chemical compound, which may be a peptidic moiety, that binds to, or complexes with, a canine 5-HT$_2$ receptor or variant thereof. Exemplary ligands include ketanserin, DOI, SCH-23390, ritanserin, risperidone, MDL-100907, eplivanserin, methiothepin, olanzapine, mesulergine, 5-hydroxytryptamine, m-CPP, α-Me-5-hydroxytryptamine, BW-723C86, RU-24969, TFMPP, 5-CT, SB-204741, and yohimbine, and labeled forms thereof. Preferred ligands are high-affinity ligands, e.g., a ligand or ligand component that has a binding affinity constant, $pK_I$ (negative log of $K_I$), for 5-HT$_2$ receptor that is 6.5 or higher.

In a preferred embodiment, the assay reagent in the method is associated with a cell expressing a canine 5-HT$_2$ receptor on the cell surface. The cell is at least one cell or a plurality of cells appropriate for the sensitivity of the detection method. Cells suitable for the present invention may be bacterial, but are preferably eukaryotic, such as yeast, insect, or mammalian. The cell can be a natural host cell for an endogenous canine 5-HT$_2$ receptor, preferably a recombinant host cell for a canine 5-HT$_2$ receptor, which expresses a high amount of a canine 5-HT$_2$ receptor on the cell surface.

In another preferred embodiment, the biological activity of the canine 5-HT$_2$ receptor or functional variant thereof can be measured by a second messenger response of the cell. For example, the biological activity of the complex can be measured by the signal transduction event triggered by activated canine 5-HT$_2$ receptor activation. This signal transduction event can be measured indirectly by means of measuring one or more changes in cellular physiology, such as cell morphology, migration, or chemotaxis, using one or more suitable methods known in the art. It can also be measured directly by measuring phosphorylation of proteins involved in the signal transduction pathway, for example, the phosphorylation of a GTP-binding protein (G protein). Methods are known in the art for measuring protein phosphorylation, for example, by using an ATP or GTP molecule that has been radiolabeled on the γ-phosphate.

A "second messenger response of a cell" refers to cellular response of the cell mediated through activation of the receptor upon binding to, or complexing with, a ligand. It may include, e.g., signal transduction event or a change in intracellular concentration of a second messenger molecule, such as proton (pH), calcium, or cAMP.

The biological activity of a canine 5-HT$_2$ receptor material or variant can also be measured by the intracellular concentration of a second messenger molecule using any of a number of suitable techniques known in the art. For example, the pH change can be measured using a pH-sensitive dye, such as Acridine Orange. The calcium concentration can be measured via optical imaging of fluorescent indicators sensitive to $Ca^{2+}$, such as fluo-3 (pentapotassium salt, cell-impermeant form; Molecular Probes) or fluo-3(AM) (an acetoxymethyl ester form of fluo-3; Teflabs) (see, for example, Liu et al., 2001, *J. Pharmacol. Exp. Ther.*, 299: 121-30) using a fluorometric imaging plate reader (FLIPR) or a confocal microscope. The cAMP concentration can be detected using a commercially available ELISA kit (FLASHPLATE cyclic AMP assay system ($^{125}$I, Cat. No: SMP001A, NEN; see also Shimomura et al., 2002, *J. Biol. Chem.*, 277: 35826-32), or via a reporter system wherein the expression of a reporter gene, such as beta-galactosidase, is under the control of a cAMP responsive element (cre) (Montminy et al., 1990, *Trends Neurosci.*, 13(5):184-8).

The test compound may be further characterized by comparing its effect on two cells, the first cell containing a biologically active canine 5-HT$_2$ receptor or functional variant thereof and the second one identical to the first, but lacking the active 5-HT$_2$ or functional variant. This technique is also useful in establishing the background noise of these assays. One of ordinary skill in the art will appreciate that this control mechanism also allows ready selection of cellular changes that are responsive to modulation of the canine 5-HT$_2$ receptor. Therefore, in a preferred embodiment, the screening method comprises the steps of: (a) contacting a first cell having a canine 5-HT$_{2A}$ receptor or a canine 5-HT$_{2B}$ receptor expressed on the cell surface with a 5-HT$_2$ receptor ligand and with a test compound; (b) determining a second messenger response in the first cell to the test compound, and comparing it with that of a control wherein the first cell is only contacted with a 5-HT$_2$ receptor ligand but not the test compound; (c) contacting a second cell with the 5-HT$_2$ receptor ligand and with a test compound, wherein the second cell is otherwise identical to the first cell except that it either does not express a canine 5-HT$_{2A}$ or does not express a canine 5-HT$_{2B}$ receptor on the cell surface; (d) determining a second messenger response of the second cell to the test compound, and comparing the second messenger response with that of a control wherein the second cell is only contacted with the 5-HT$_2$ receptor ligand but not the test compound; and (e) comparing the comparison result of (b) with that of (d).

There are a number of ways to obtain two cells that are otherwise identical except that one cell expresses either a canine 5-HT$_2$ receptor on its cell surface and the other cell does not. In one embodiment, the first cell is a recombinant host cell for a canine 5-HT$_2$ receptor that constitutively expresses the canine 5-HT$_2$ receptor on its cell surface, and the second cell is the parent cell from which such recombinant host cell is constructed. In another embodiment, a recombinant host cell for the canine 5-HT$_2$ receptor is constructed such that its expression on the cell surface is under the control of an inducible promoter. The first cell is the recombinant cell grown under inducible conditions that allow the expression of a canine 5-HT$_2$ receptor on the cell surface, and the second cell is the recombinant cell grown under non-inducible conditions that do not allow the expression of the canine 5-HT$_2$ receptor. In yet another embodiment, the first cell is a native host cell for at least one canine 5-HT$_2$ receptor that expresses the polypeptide on its cell surface, and the second cell is a mutant cell derived from the native host, wherein the at least one canine 5-HT$_2$ receptor gene has been inactivated through mutagenesis. Standard molecular biology methods can be used to construct a recombinant host cell for a canine 5-HT$_2$ receptor, or to inactivate a canine 5-HT$_2$ receptor gene.

In another embodiment, the present invention provides a method of identifying a compound that increases or decreases the activity of a receptor/ligand complex, comprising the steps of: (a) contacting an isolated membrane preparation comprising a 5-HT$_2$ receptor with a ligand or an active fragment thereof with a test compound, and with a GTP molecule that has been labeled on the γ-phosphate; (b) determining the amount of labeling bound to the membrane preparation; and (c) comparing the amount of labeling in (b) with that of a control wherein the membrane preparation is only contacted with the ligand or the active fragment thereof and the labeled GTP but not the test compound.

A variety of labels can be used to label the GTP molecule on the γ-phosphate, such as a fluorescent molecule or a radioactive isotope, such as $^{35}$S, $^{32}$P, and the like.

In yet another embodiment, the present invention provides a method of identifying a compound that binds to a 5-HT$_2$ receptor, comprising the steps of: (a) contacting a biologically active canine 5-HT$_2$ receptor or variant thereof with a test compound, and with a labeled ligand or an active fragment thereof; (b) measuring the amount of the labeled ligand or the fragment thereof that binds to the receptor; and (c)

comparing the measured amount of (b) with that of a control, wherein the receptor is only contacted with a labeled ligand or the fragment thereof, but not the test compound. The amount of the labeled ligand or fragment thereof that binds to the receptor can be measured by first separating the unbound labeled ligand or fragment from the receptor, and then measuring the amount of labeling that is associated with the receptor.

Separation of the receptor protein from unbound labeled ligand or fragments thereof can be accomplished in a variety of ways. Conveniently, the 5-HT$_2$ material may be immobilized on a solid substrate, from which the unbound ligand can be easily separated. The solid substrate can be made of a variety of materials and in a variety of shapes, e.g., microtiter plate, microbead, dipstick, and resin particle. The substrate preferably is chosen to maximize signal-to-noise ratio, primarily to minimize background binding, as well as for ease of separation and cost. Separation can be effected by, for example, removing a bead or dipstick from a reservoir, emptying or diluting a reservoir such as a microtiter plate well, or rinsing a bead, particle, chromatographic column or filter with a wash solution or solvent. The separation step preferably includes multiple rinses or washes. For example, when the solid substrate is a microtiter plate, the wells can be washed several times with a washing solution, e.g., that includes those components of the incubation mixture that do not participate in specific bindings, such as salts, buffer, detergent, non-specific protein, etc. Where the solid substrate is a magnetic bead, the beads can be washed one or more times with a washing solution and isolated using a magnet.

The canine 5-HT$_2$ receptor material may be immobilized on a solid substrate using a number of methods. In one embodiment, a fusion protein can be provided which adds a domain that allows the canine 5-HT$_2$ protein to be bound to a matrix. For example, a glutathione-S-transferase fusion protein can be adsorbed onto glutathione sepharose beads (Sigma Chemical, St. Louis, Mo.) or glutathione derivatized microtiter plates, which are then combined with the test compound and the labeled ligand, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or the labeled ligand to 5-HT$_2$ material can be determined using standard techniques.

Other techniques for immobilizing proteins on matrices can also be used in the screening assays of the invention. For example, the canine 5-HT$_2$ material can be immobilized utilizing conjugation of biotin and streptavidin. Biotinylated polypeptide can be prepared from biotin-NHS (N-hydroxysuccinimide) using techniques known in the art (e.g., biotinylation kit available from Pierce Chemicals, Rockford, Ill.), and immobilized in the wells of streptavidin-coated 96-well plates (Pierce Chemicals). Alternatively, antibodies reactive with the 5-HT$_2$ material but which do not interfere with binding of it to the ligand or test compound can be attached to the wells of the plate, and 5-HT$_2$ material can then be trapped in the wells by antibody conjugation.

A variety of labels can be used to label the ligand or fragments thereof, such as those that provide direct detection (e.g., radioactivity, luminescence, optical or electron density) or indirect detection (e.g., epitope tag such as the FLAG epitope, or enzyme tag such as horseradish peroxidase).

Other embodiments, features, and advantages of the invention will become apparent by reference to the following illustrative examples.

EXAMPLES

As described in the examples below, both the canine 5-HT$_{2A}$ and 5-HT$_{2B}$ receptors have now been cloned. The canine and human 5-HT$_{2A}$ receptors share 93% amino acid homology. The canine and human 5-HT$_{2B}$ receptors are also highly conserved (87% homology), with the exception of the carboxyl termini, where the canine protein is 60 amino acids shorter. Pharmacological comparisons of recombinant canine and human 5-HT$_{2A}$ and 5-HT$_{2B}$ receptors using radioligand binding and FLIPR based Ca$^{2+}$ assays showed no major differences in affinity or functionality between the human and canine receptor subtypes for the 19 serotoninergic ligands investigated.

Example 1

Cloning of Canine 5-HT$_{2A}$ and 5-HT$_{2B}$ Receptor cDNA

A 500 bp sequence of dog 5-HT$_{2A}$ DNA was identified from NCBI GenBank (Genbank Accession No. Y16134) using human 5-HT$_{2A}$ sequence (GenBank accession number AF498982) as the query. The resulting dog 5-HT$_{2A}$ sequence was used to design primers for cloning of the full length cDNA using the rapid amplification of cDNA ends (RACE) method using dog brain cDNA as the template, which was synthesized using a RACE cDNA kit from BD Biosciences (Palo alto, Calif.). A dog 5-HT$_{2A}$ gene specific primer, SEQ ID NO.:1 (5'-TCT AGC GAG ATG GCG CAC AGG TGC ATG ATG-3'), was used for the 5' end RACE. A dog 5-HT$_{2A}$ gene specific primer, SEQ ID NO.:2 (5'-CCA CCT TGT GTG TGA GTG ATC CTG GCA CAC-3'), was used for the 3' end RACE. The resulting cDNA was sequenced to obtain the complete coding region for dog 5-HT$_{2A}$. Two primers (forward primer, SEQ ID NO.:3: 5'-ACT AGA CTC GAG GCC ACC ATG GAT GTC CTC TTT GAG GAT AAT GCT-3', and reverse primer, SEQ ID NO.:4: 5'-ACT AGA GCG GCC GCT CAC ACA CAG CTA ACC TTT TCA TTC ACT GT-3') were used to amplify the full length dog 5-HT2A cDNA from dog brain cDNA. The resulting 5-HT$_{2A}$ full length cDNA was cloned into the pCIneo vector (Promega, Madison, Wis.) and the insert region sequenced to confirm the sequence identity (accession number AY832858). The results showed that the dog 5-HT$_{2A}$ cDNA encodes 470 amino acids, which is one amino acid less than human 5-HT$_{2A}$. Amino acid sequence comparison between the dog and human 5-HT$_{2A}$ receptors showed that they share about 93% homology (FIG. 1).

A dog 5-HT$_{2B}$ gene sequence was identified from the dog genome sequence (Genbank Accession No. AAEX01019724) using the human 5-HT$_{2B}$ DNA sequence (GenBank accession number AY136751) as the query. Two primers (forward primer, SEQ ID NO.:5: 5'-AGT AGA GAA TTC GCC ACC ATG GCC ATC TCT TAT AGA ATA TCA GAA C-3' and reverse primer, SEQ ID NO.:6: 5'-ACT AGA GCG GCC GCA TTA GGT GAA TAC CTC TAT TCC TTC TA-3') were then designed according to the dog 5-HT$_{2B}$ genomic sequence to amplify the dog 5-HT$_{2B}$ cDNA using dog brain cDNA as the template. The resulting DNA was cloned into pCIneo vector and the insert region was sequenced to confirm the sequence identity. The sequencing results indicated that the dog 5-HT$_{2B}$ cDNA (accession number AY832859) bears 87% homology to the human 5-HT$_{2B}$.

While the human 5-HT$_{2B}$ has 481 amino acids, the dog 5-HT$_{2B}$ gene only encodes 435 amino acids, missing the C-terminal tail corresponding to the last 60 amino acids of the human 5-HT$_{2B}$ (FIG. 2). Using the RACE technique, the canine 5-HT$_{2B}$ cDNA sequence was further investigated using tissue from two additional dogs from different sources; the same sequence was identified.

Example 2

Ligand Binding Profile of Recombinant Canine 5-HT$_{2A}$ and 5-HT$_{2B}$ Receptors In order to investigate the ligand binding profiles of the canine 5-HT$_{2A}$ and 5-HT$_{2B}$ receptors, saturation binding studies and Scatchard analysis as well as ligand displacement studies were performed using isolated membranes from COS-7 cells that were transfected with canine 5-HT$_{2A}$ and 5-HT$_{2B}$ receptors.

The following compounds were used in the canine 5-HT$_{2A}$ receptor and canine 5-HT$_{2B}$ receptor ligand binding studies and ligand displacement studies described below: [$^3$H]-ketanserin (76.5 Ci/mmol), obtained from PerkinElmer Life Science (Boston, Mass.); [$^3$H]-mesulergine (97 Ci/mmol), obtained from Amersham Bioscience (UK); risperidone (U.S. Pat. No. 4,804,663), ritanserin (WO 94/27991), ketanserin (U.S. Pat. No. 4,335,127), olanzapine (WO 96/30374), eplivanserin (WO 2002053140 and Rinaldi-Carmona et al., 1992, J. Pharmacol. Exp. Ther, 262(2):759-768), and MDL-100907 (WO 91/18602 and Sorensen et al., 1993, J. Pharmacol. Exp. Ther., 266(2):684-691), synthesized in-house; SB-204741 (N-(1-methyl-5-in-dolyl)-N'-(3-methyl-5-isothiazolyl) urea), 5-HT (5-hydroxytryptamine), 5-CT (5-carboxyamidotryptamine), α-Me-5-HT (2-methyl-5-hydroxytryptamine), mesulergine, yohimbine, and methiothepin, obtained from Sigma RBI (St Louis, Mich.); and BW-723C86 (1-{5-(2-thienyl-methoxy)-1H-3-indolyl}propan-2-amine), m-CPP (1-(3-chlorophenyl)piperazine, DOI (1-(2,5-dimethoxy-4-iodophenyl)-2-aminopropane), RU-24969 (5-methoxy-3(1,2,3,6-tetrahydro-4-pyridiny)-1H-indole), SCH-23390 (R-(+)-7-chloro-8-hydroxy-3-methyl-1-phenyl-2,3,4,5-tetrahydro(1H)-3-benzapine), and TFMPP (N-(3-trifluoromethyl-henyl)piperazine), obtained from Tocris Cookson (Bristol, UK).

COS-7 cells were grown in Dulbecco's Modified Eagle's Medium (DMEM, Invitrogen, Carlsbad, Calif.) with 10% fetal bovine serum and transfected with either the canine 5-HT$_{2A}$ or the 5-HT$_{2B}$ receptor cDNA plasmid using Fugeneg (Roche, Indianapolis) as directed by the manufacturer. Two days after transfection with the vectors described above, the COS-7 cells were detached with phosphate buffered saline plus 5 mM EDTA and centrifuged at 1000 rpm for 5 min. The pellets were stored at −80° C. Membranes were homogenized in 50 mM Tris, 1 mM EDTA and centrifuged at 20,000×g for 25 min. The resulting pellet was resuspended in 50 mM Tris, 0.5 mM EDTA, 5 mM MgCl$_2$, pH 7.4 (Roth et al., 2000) and aliquotted into 96-well plates (Greiner Bio-One, Frickenhausen, Germany). Nonspecific binding of the radioligands was estimated in the presence of 1 μM risperidone for both 5-HT$_{2A}$ and 5-HT$_{2B}$. For ligand concentration binding isotherms, 10-12 concentrations of the radioligand ([$^3$H]5-HT) in a range of 0.1 nM to 20 nM were used. Experiments were repeated independently at least three times. Human 5-HT$_{2A}$ and 5-HT$_{2B}$ receptors were evaluated for comparison. NIH 3T3 cells stably expressing the recombinant human 5-HT$_{2A}$ receptor were grown in DMEM with 10% fetal bovine serum, 1% penicillin-streptomycin and 600 μg/ml G418. CHO cells stably expressing the recombinant human 5-HT$_{2B}$ receptor were grown in DMEM/F-12 nutrient mixture supplemented with 10% FBS, 1% penicillin-streptomycin and 400 ug/ml G418.

Incubations of the membranes with the radioligands were each run for 60 min at room temperature in a volume of 200 μl and then harvested by filtration through GF/B filters (Packard, Meriden, Conn.) pretreated with 0.3% polyethylenimine. The filters were washed five times with ice-cold buffer and dried in a 50° C. oven. A 35 μl quantity of Microscint 0 (Packard) was added to each well, and the plates were then counted on Packard TopCount. Ligand concentration binding isotherms and sigmoidal inhibition curves were generated and fitted using nonlinear regression analysis using GraphPad Prism software (San Diego, Calif.). The B$_{max}$ and apparent K$_D$ values of the radioligands and pIC$_{50}$ of the inhibitor were free parameters for the curve fitting. Apparent K$_I$ values were calculated as K$_I$=IC$_{50}$/(1+C/K$_D$), where C is concentration of the radioligand. Data were expressed as mean±S.E.M. Final protein content was assayed according to the method described in the BCA protein assay kit (Pierre).

Figure 3B:
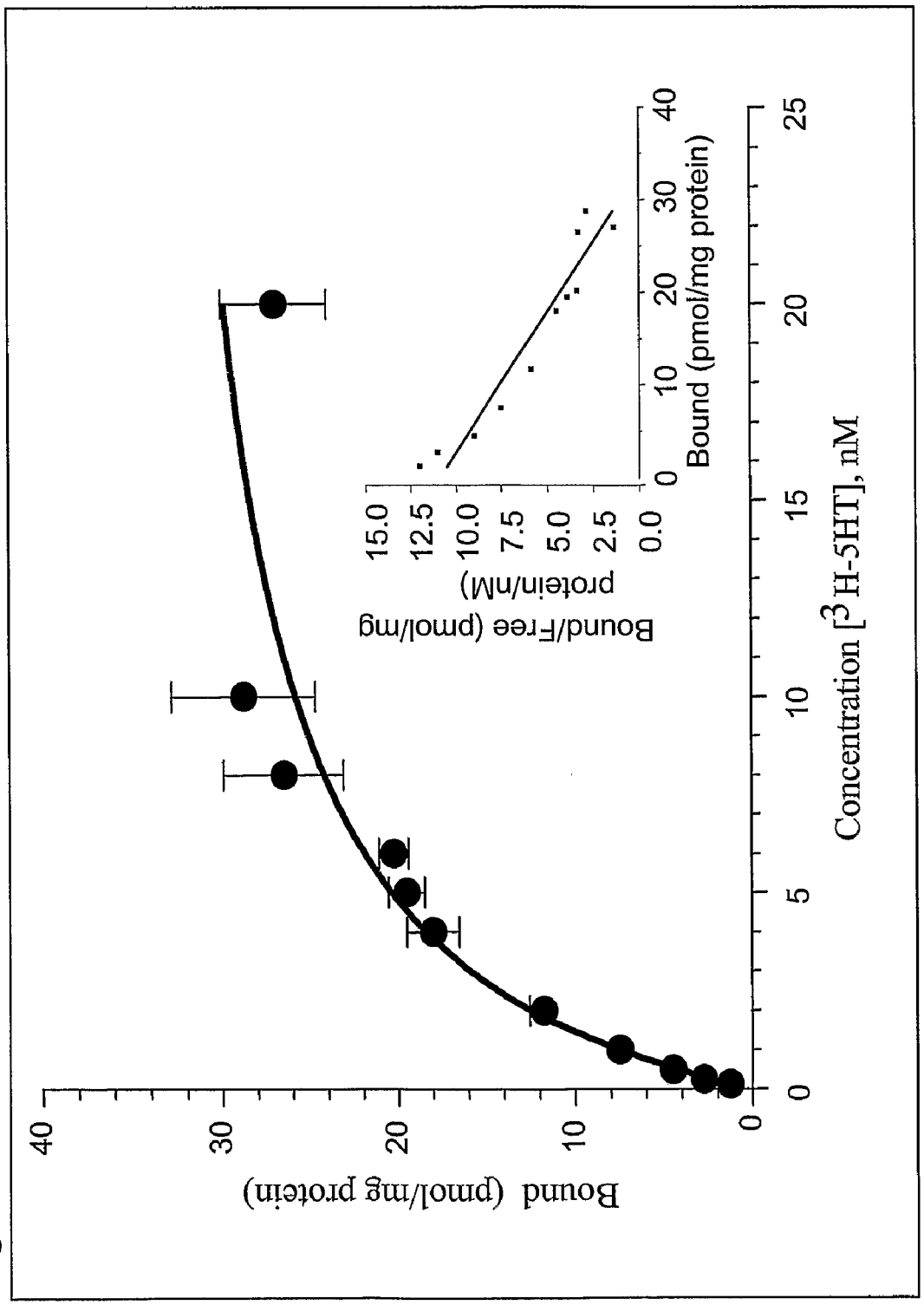

The saturation binding and Scatchard analyses of the data obtained, shown in FIGS. 3A and 3B, demonstrate that membranes obtained from COS-7 cells transiently transfected with the canine 5-HT$_{2A}$ (FIG. 3A) or canine 5-HT$_{2B}$ (FIG. 3B) showed a single population of high affinity binding sites for [$^3$H]5-HT. The K$_D$ and B$_{max}$ values are given in Table 1 below. Values for the human 5-HT$_{2A}$ and human 5-HT$_{2B}$ receptors are also given for comparison in Table 1 and were found to be within a similar range to the values obtained for the canine receptors.

TABLE 1

Apparent equilibrium dissociation constant (K$_D$) and maximum number of binding sites (B$_{max}$) values measured with [$^3$H]-5-HT for binding to canine (c) and human (h) 5-HT$_{2A}$ or 5-HT$_{2B}$ receptors (in recombinant cell membranes derived from the indicated cell lines). Values are mean ± S.E.M. (n = 3 to 6)

| | Species: | | | |
|---|---|---|---|---|
| | canine | human | canine | human |
| | Receptor subtype: | | | |
| | 5-HT$_{2A}$ | 5-HT$_{2A}$ | 5-HT$_{2B}$ | 5-HT$_{2B}$ |
| | Cell line: | | | |
| | COS-7 | NIH3T3 | COS-7 | CHO |
| K$_D$ (nM) | 3 ± 0.60 | 1.75 ± 0.17 | 3.90 ± 0.82 | 2.67 ± 0.54 |
| B$_{max}$ (pmol/mg protein) | 13.5 ± 4.50 | 25.5 ± 4.58 | 30.75 ± 4.05 | 36.67 ± 7.12 |

For competition binding studies, COS-7 cells were cultured, transfected with either canine 5-HT$_{2A}$ or 5-HT$_{2B}$ receptor-encoding expression vectors, and membranes obtained as described above. Nineteen serotonergic compounds (nine putative agonists and ten putative antagonists) were assayed for their ability to displace [$^3$H]-ketanserin nM (canine 5-HT$_{2A}$, K$_D$=1.3±0.12 nM) or 4 nM [$^3$H]-mesulergine (canine 5-HT$_{2B}$, K$_D$=5.43±0.69 nM) from the membranes obtained from the transfected COS-7 cells. The compounds that were tested were added at seven different concentrations ranging from 0.01 nM to 10 μM. Similar competition binding experiments were performed in parallel using membranes obtained from NIH3T3 or CHO cells expressing human 5-HT$_{2A}$ or human 5-HT$_{2B}$ receptors, respectively. The affinity constants (pK$_I$) derived from these experiments are provided in Table 2 below:

TABLE 2

Affinity constants (pK$_I$) of serotonergic ligands for inhibition of [$^3$H]-ketanserin or [$^3$H]-mesulergine binding to membranes derived from COS-7, CHO or NIH3T3 cells expressing recombinant canine (c) or human (h) 5-HT$_{2A}$ or 5-HT$_{2B}$ receptors. PK$_I$ values are the mean ± S.E.M of 3-8 independent experiments.

| Receptor: | | | | | |
|---|---|---|---|---|---|
| c5-HT$_{2A}$ | h5-HT$_{2A}$ | c5-HT$_{2B}$ | h5-HT$_{2B}$ | | |
| Cell line: | | | | | |
| COS-7 | NIH3T3 | COS-7 | CHO | Ratio c5-HT$_{2A}$ vs. h5-HT$_{2A}$ | Ratio c5-HT$_{2B}$ vs. h5-HT$_{2B}$ |
| Radioligand: | | | | | |
| [$^3$H]-ketanserin | [$^3$H]-mesulergine | [$^3$H]-ketanserin | [$^3$H]-mesulergine | | |

Agonists

| | | | | | |
|---|---|---|---|---|---|
| 5-HT | 6.75 ± 0.11 | 6.96 ± 0.06 | 8.52 ± 0.08 | 8.35 ± 0.06 | 1.63 | 0.67 |
| DOI | 7.92 ± 0.12 | 8.29 ± 0.12 | 7.88 ± 0.15 | 7.82 ± 0.08 | 2.37 | 0.87 |
| m-CPP | 6.71 ± 0.01 | 7.06 ± 0.07 | 7.68 ± 0.05 | 7.54 ± 0.07 | 2.23 | 0.73 |
| SCH-23390 | 7.79 ± 0.14 | 7.87 ± 0.12 | 6.51 ± 0.12 | 6.56 ± 0.04 | 1.21 | 1.12 |
| α-Me-5-HT | 6.76 ± 0.28 | 7.12 ± 0.11 | 8.54 ± 0.09 | 8.50 ± 0.09 | 2.31 | 0.91 |
| BW-723C86 | 6.20 ± 0.19 | 6.41 ± 0.20 | 7.58 ± 0.06 | 8.11 ± 0.06 | 1.60 | 3.36 |
| TFMPP | 6.67 ± 0.12 | 7.06 ± 0.11 | 7.38 ± 0.09 | 7.40 ± 0.05 | 2.45 | 1.04 |
| RU-24969 | 5.90 ± 0.14 | 6.00 ± 0.14 | 7.89 ± 0.41 | 7.61 ± 0.07 | 1.26 | 0.53 |
| 5-CT | 5.64 ± 0.07 | 5.94 ± 0.04 | 7.13 ± 0.07 | 7.21 ± 0.08 | 1.99 | 1.20 |

Antagonists

| | | | | | |
|---|---|---|---|---|---|
| Ritanserin | 8.12 ± 0.06 | 8.49 ± 0.06 | 8.40 ± 0.01 | 8.34 ± 0.07 | 2.33 | 0.87 |
| Risperidone | 8.50 ± 0.13 | 9.04 ± 0.16 | 7.35 ± 0.24 | 7.59 ± 0.05 | 3.54 | 1.73 |
| MDL-100907 | 8.76 ± 0.06 | 9.12 ± 0.01 | 5.90 ± 0.05 | 5.96 ± 0.05 | 2.32 | 1.16 |
| Eplivanserin | 9.00 ± 0.16 | 9.70 ± 0.08 | 5.72 ± 0.04 | 5.85 ± 0.06 | 4.99 | 1.36 |
| SB-204741 | <5 | <5 | 6.74 ± 0.08 | 6.92 ± 0.01 | 1.00 | 1.50 |
| Mesulergine | 7.04 ± 0.14 | 7.64 ± 0.14 | 7.77 ± 0.15 | 8.06 ± 0.06 | 4.01 | 1.92 |
| Yohimbine | 5.01 ± 0.01 | 5.58 ± 0.01 | 7.09 ± 0.12 | 7.18 ± 0.07 | 3.68 | 1.25 |
| Methiothepin | 8.45 ± 0.17 | 8.98 ± 0.08 | 8.12 ± 0.16 | 8.38 ± 0.03 | 3.42 | 1.82 |
| Ketanserin | 7.84 ± 0.09 | 8.54 ± 0.16 | 6.20 ± 0.14 | 6.38 ± 0.14 | 4.95 | 1.51 |
| Olanzapine | 7.97 ± 0.15 | 8.49 ± 0.19 | 7.46 ± 0.10 | 7.97 ± 0.11 | 3.30 | 3.24 |

Figure 4A:
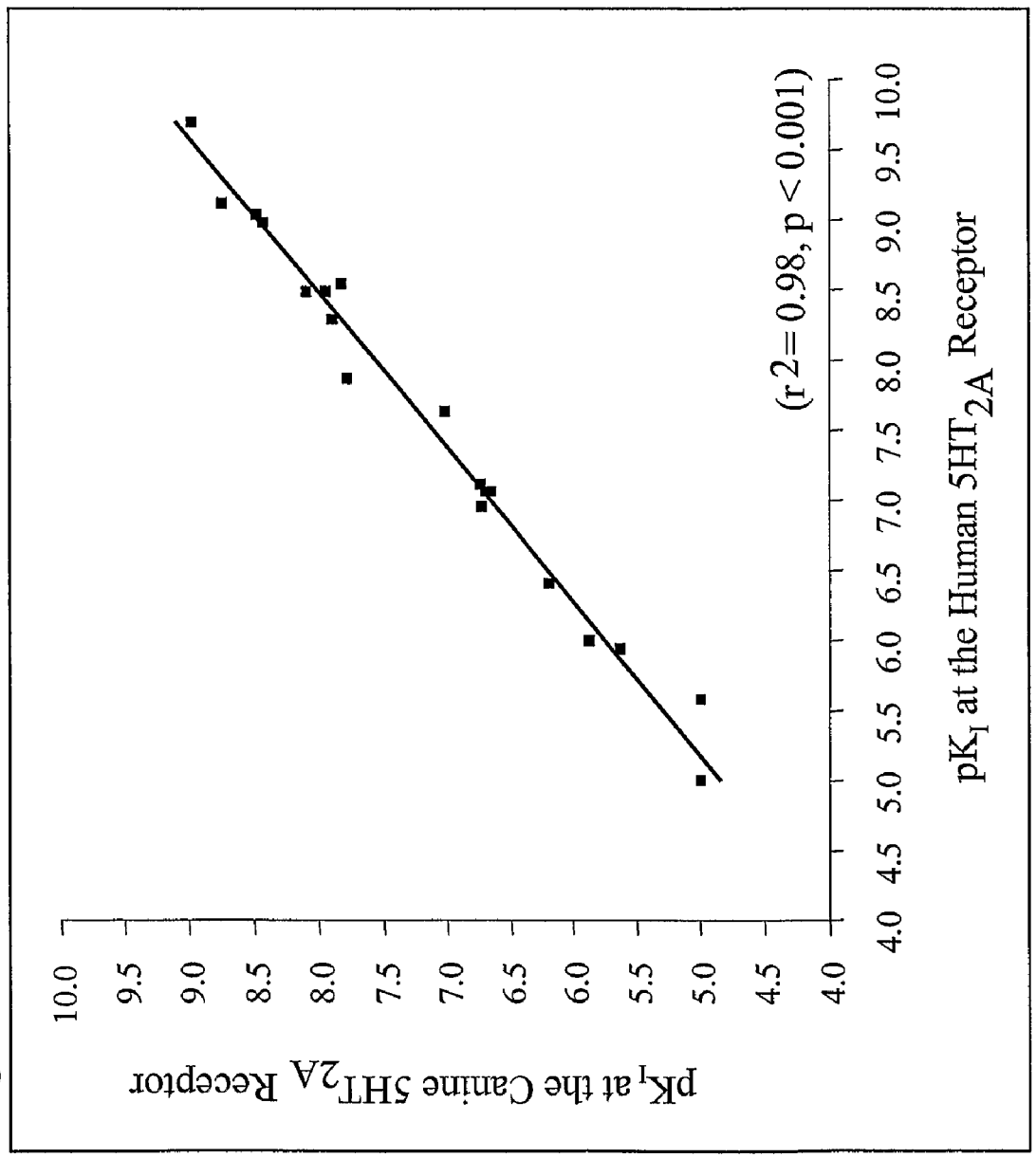
FIGS. 4A-4D show regression analyses of binding affinity constants (pK$_i$ values) of serotonergic ligands (see Table 2) at the cloned canine 5-HT$_{2A}$ and 5-HT$_{2B}$ receptor with human 5-HT$_{2A}$ and 5-HT$_{2B}$ receptors.
Figure 4B:
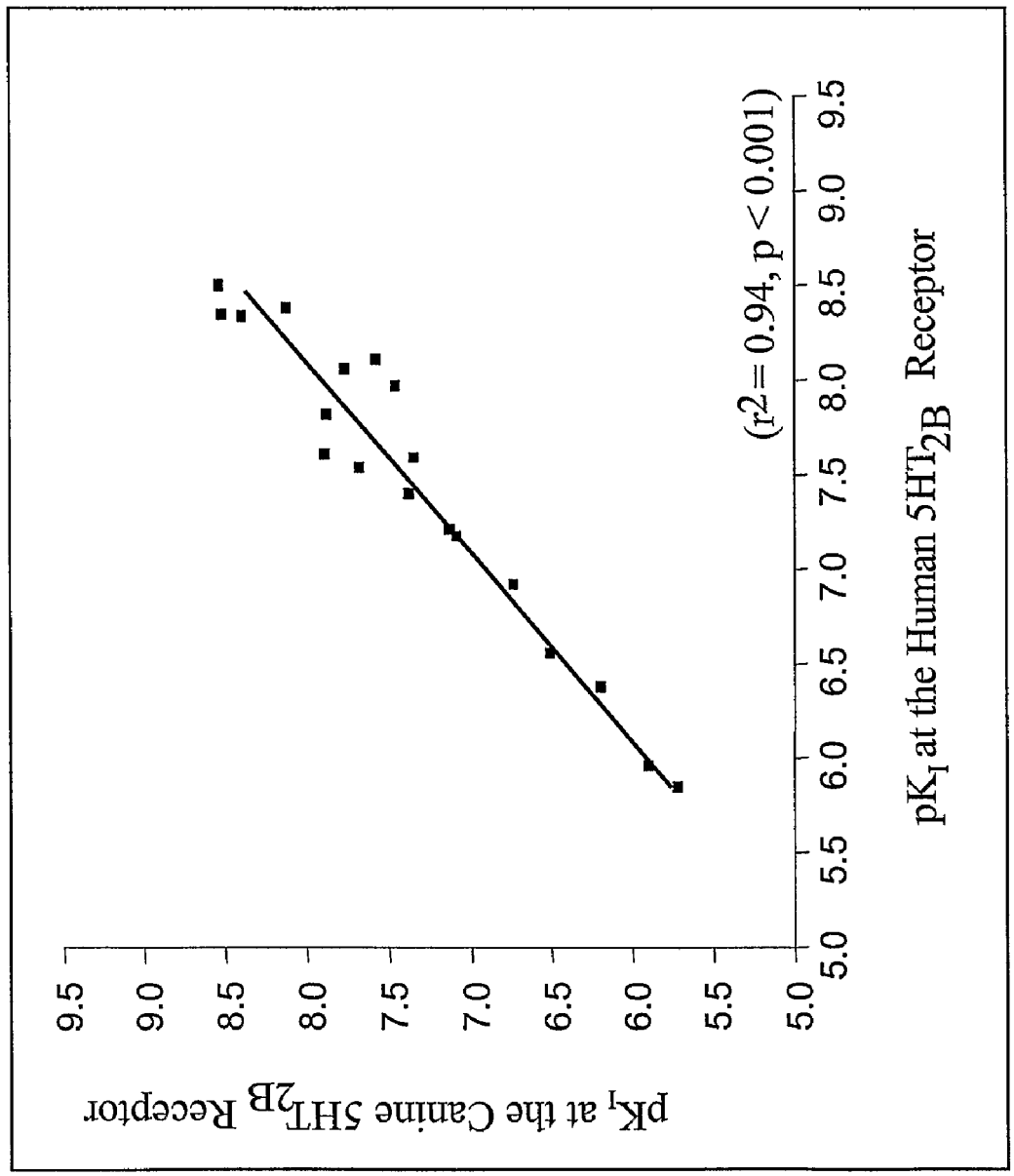
Figure 4C:
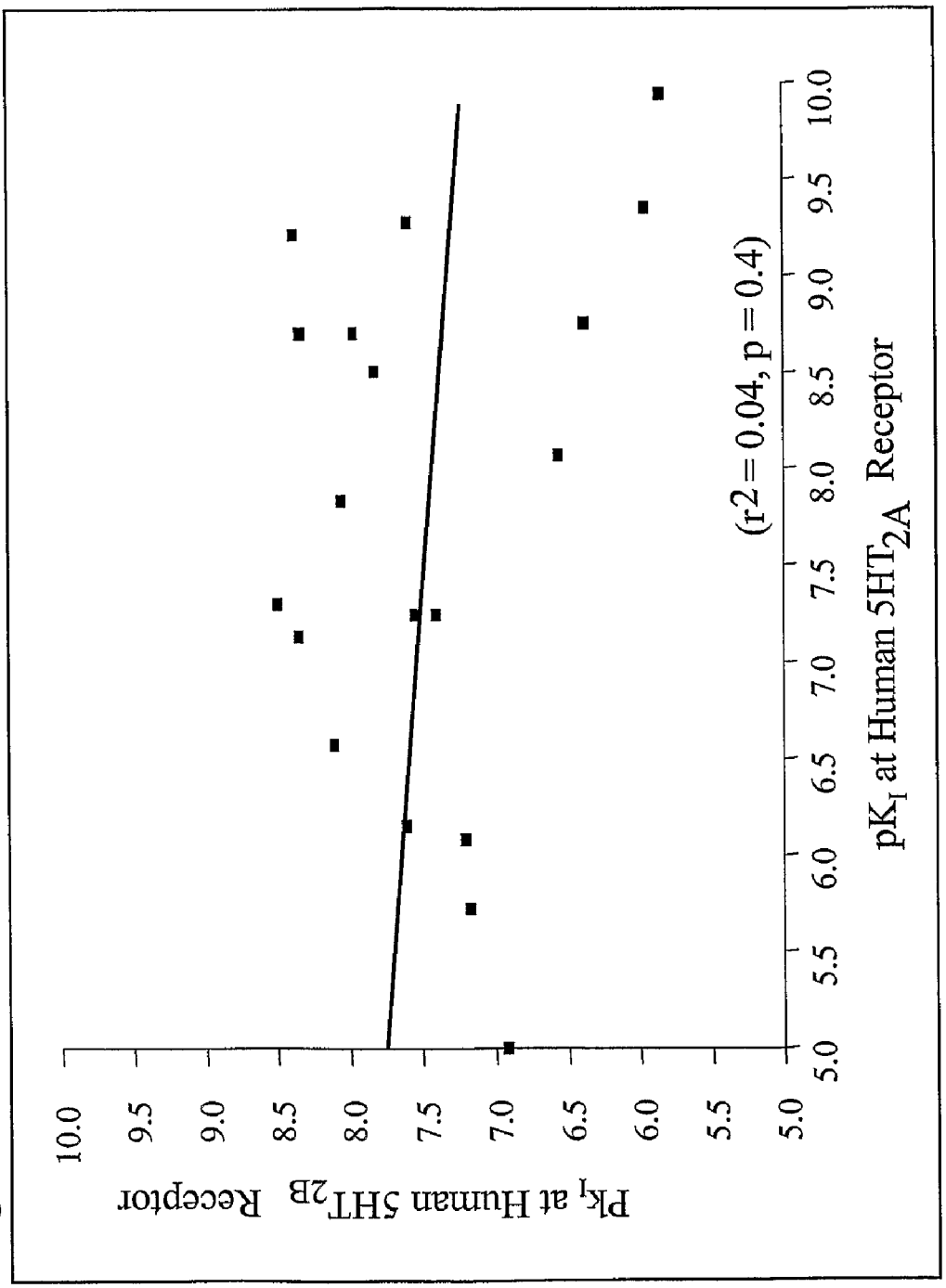
Figure 4D:
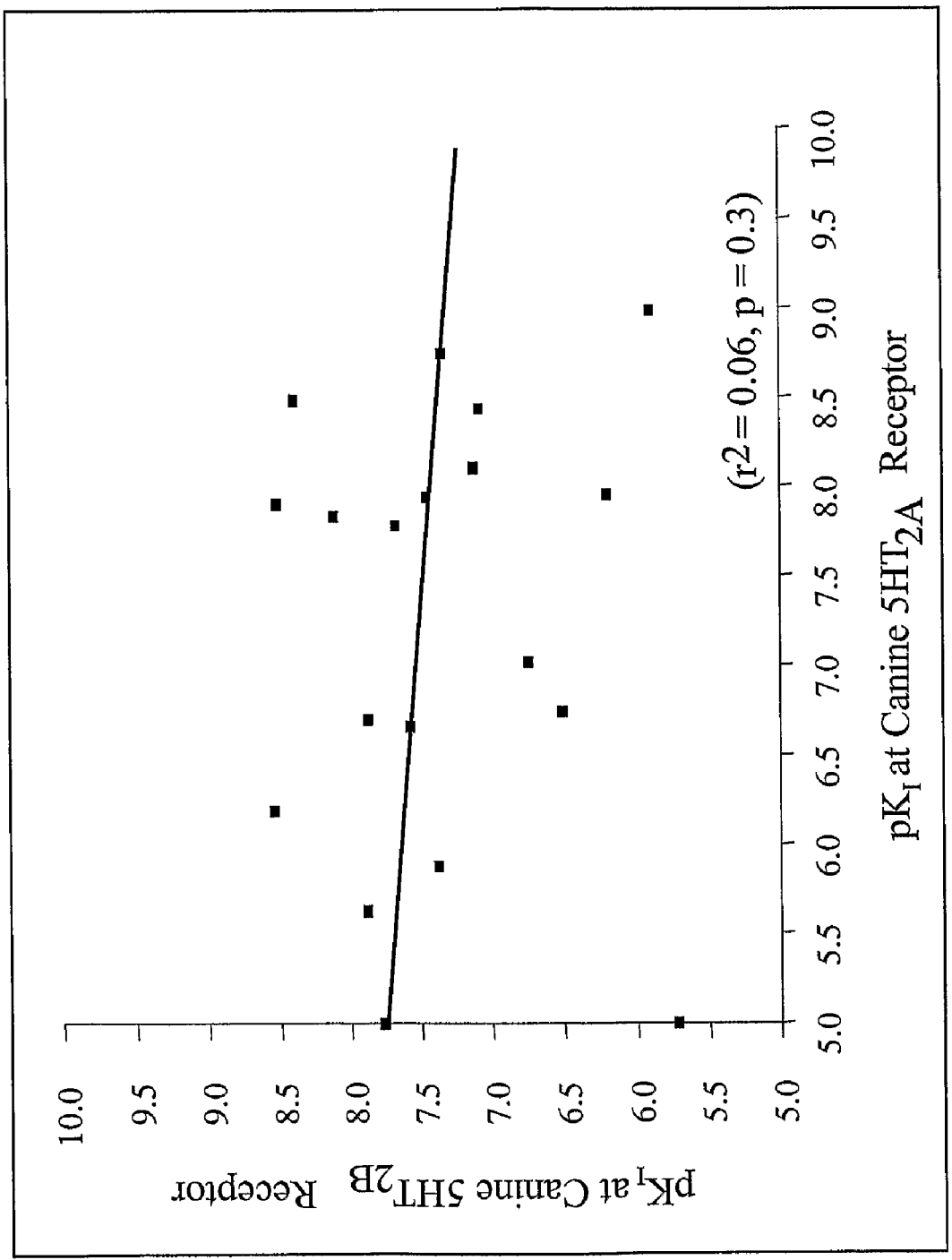

In FIGS. 4A-4D, the pK$_1$ values of the 19 serotonergic compounds obtained with membranes from the cloned canine 5-HT$_{2A}$ or canine 5-HT$_{2B}$ receptors are plotted against pK$_I$ values obtained with the same compounds using membranes from cells expressing the cloned human 5-HT$_{2A}$ or human 5-HT$_{2B}$ receptors. The affinity constants at the canine 5-HT$_{2A}$ receptor showed high correlation with those at the human 5-HT$_{2A}$ receptor (FIG. 4A). Similarly, affinity constants at the canine 5-HT$_{2B}$ receptor showed high correlation with those at the human 5-HT$_{2B}$ receptor (FIG. 4B). In contrast, the correlation at the canine 5-HT$_{2A}$ with canine 5-HT$_{2B}$ receptor was much weaker (FIG. 4C). Similarly low correlation was obtained between the human 5-HT$_{2A}$ and human 5-HT$_{2B}$ (FIG. 4D). Compounds known to display significant selectivity for human 5-HT$_{2A}$ receptor versus human 5-HT$_{2B}$ receptor (risperidone, MDL100907, eplivanserin, ketanserin) were found to display a similar selectivity profile on the canine receptor subtypes (Table 2). Similarly, compounds known to display significant selectivity for human 5-HT$_{21}$ receptor versus human 5-HT$_{2A}$ receptor (α-Me-5-HT, BW-723C86, SB-2014741, yohimbine) were found to display a similar selectivity profile on the canine receptor subtypes (Table 2).

Example 3

Functional Characterization of Recombinant Canine 5-HT$_{2A}$ and 5-HT$_{2B}$ Receptors To investigate the in vitro functional properties of the canine 5-HT$_{2A}$ and canine 5-HT$_{2B}$ receptors, the Fluorometric Imaging Plate Reader (FLIPR) was used, which integrates drug addition and Ca$^{2+}$ fluorescence measurements, allowing rapid detection of Ca$^{2+}$ following receptor activation. Human 5-HT$_{2A}$ and 5-HT$_{2B}$ receptors were also included in this study for comparison.

HEK-293 cells were cultured in DMEM with 10% fetal bovine serum, 1% penicillin-streptomycin, 10 mM HEPES, and sodium pyruvate in 10 cm tissue culture dishes. Canine 5-HT$_{2A}$ and 5-HT$_{2B}$ cDNAs were transiently transfected into HEK-293 cells using Lipofectamine (Invitrogen, Carlsbad, Calif.) as directed by the manufacturer. Forty-eight hours after transfection, the cells were detached with phosphate-buffered saline plus 10 mM EDTA, washed with cold serum free DMEM/F-12 and dye-loaded with 4 μM Fluo-3AM in serum-free DMEM/F-12 with 2.5 mM probenecid. Dye-loaded cells were plated onto 96-well ViewPlates (Packard, Meriden, Conn.) and incubated at 37° C. and 5% CO$_2$ for one hour. Once dye-loaded, dye media was replaced with serum-free DMEM/F-12. For antagonist potency determinations, cells were pre-incubated with compounds (diluted in DMEM/F-12) for 10 minutes before agonist stimulation. Ligand-induced Ca$^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the EC$_{50}$ value. Relative efficacy values are the corresponding fraction of the response elicited by the compounds compared to 10 μM 5-HT. Antagonistic potency values were converted to apparent pK$_B$ values using a modified Cheng-Prusoff correction. Apparent $pK_B = -\log IC_{50}/1+[\text{conc agonist}/EC_{50}]$. Data are expressed as mean±S.E.M.

Figure 5A:
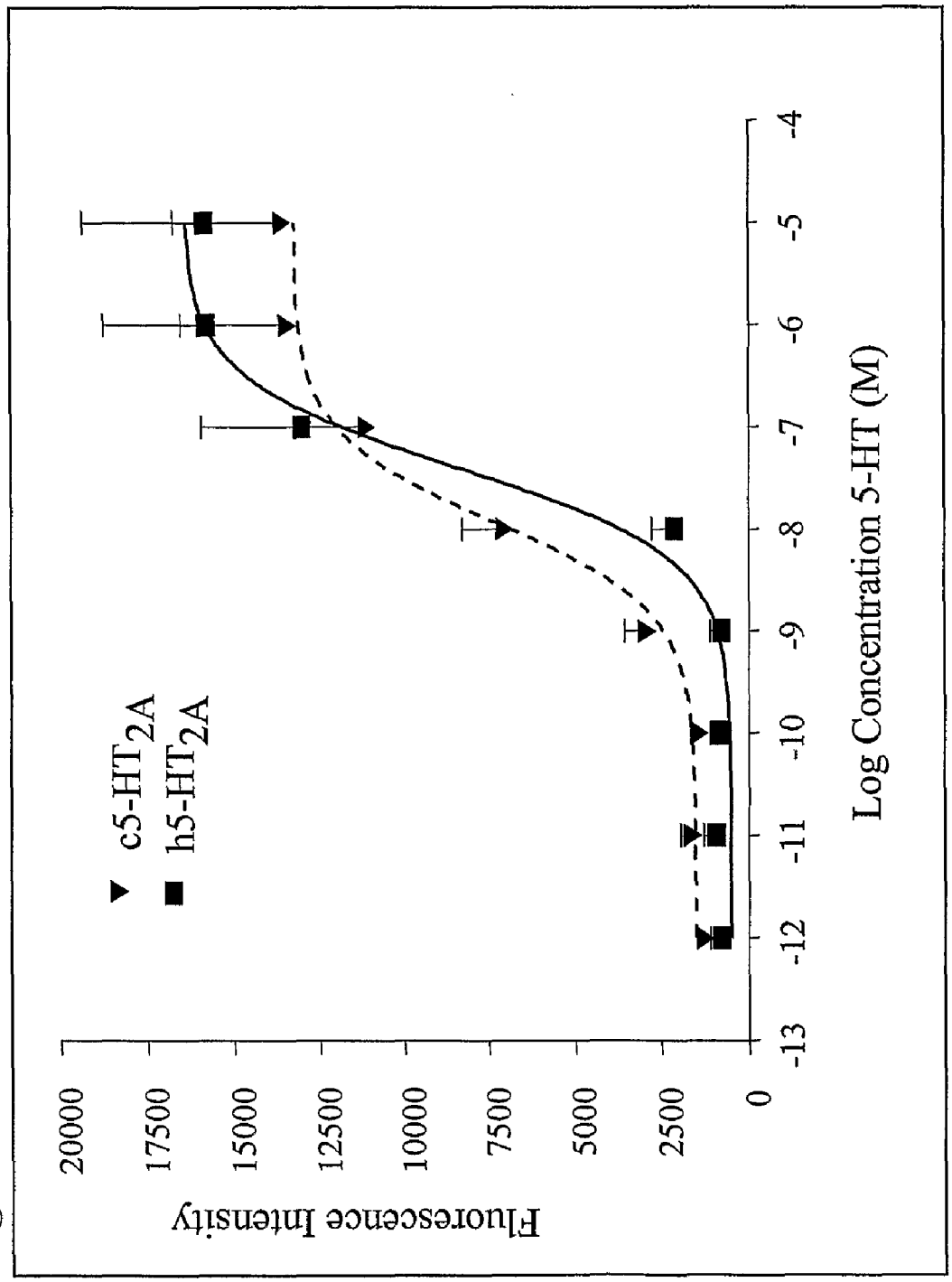
FIGS. 5A and 5B depict Ca2+ concentration response curves of 5-HT at human and canine 5-HT$_{2A}$ and 5-HT$_{2B}$ receptors, respectively.
Figure 5B:
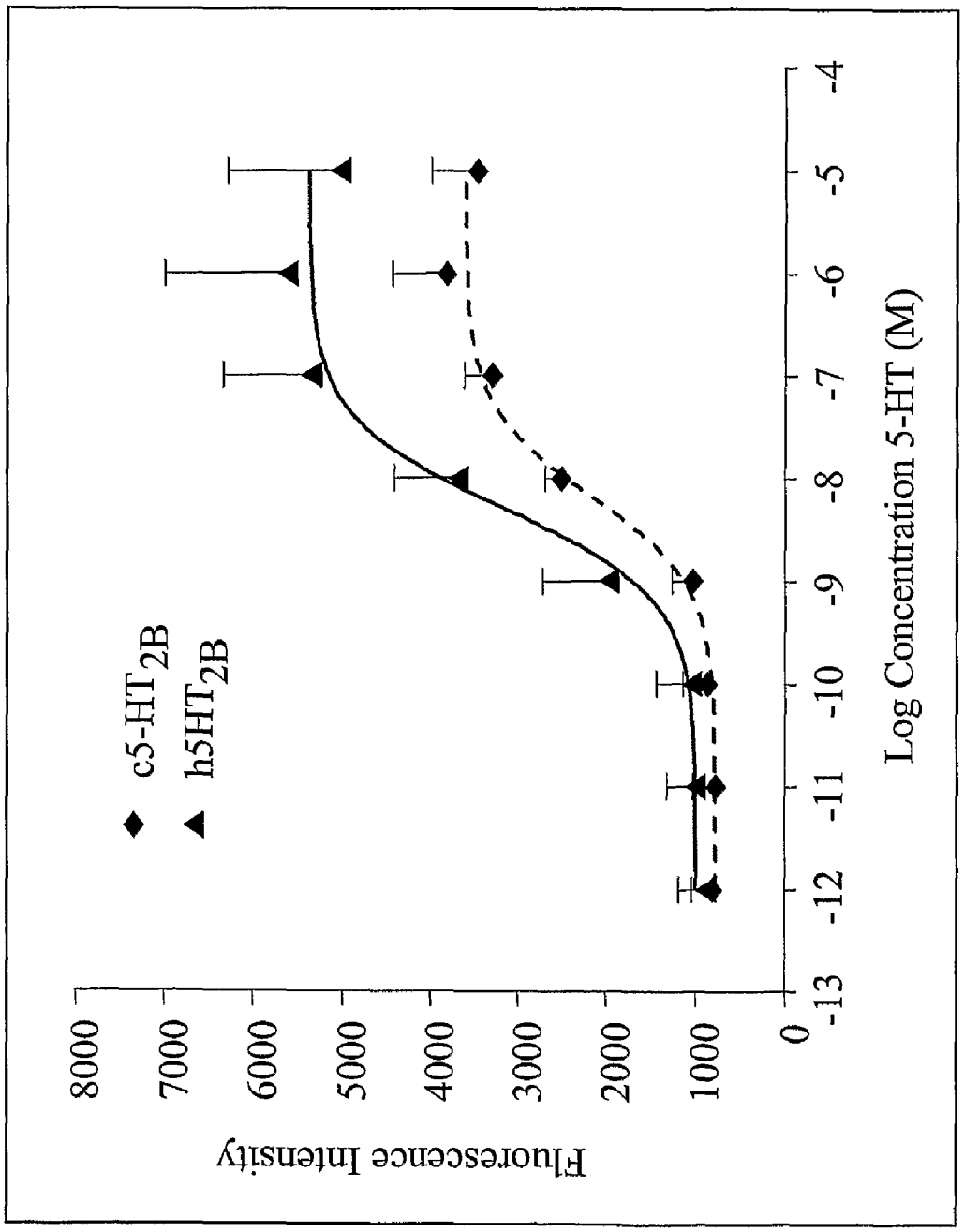

5-HT stimulated a $Ca^{2+}$ response in cells transfected with canine 5-HT$_{2A}$ (HEK-293), human 5-HT$_{2A}$ (NIH3T3), canine 5-HT$_{2B}$ (HEK-293) or human 5-HT$_{2B}$ (CHO) (FIGS. 5A and 5B). No signal to 5-HT was obtained from non-transfected HEK-293, CHO or NIH3T3 cells that underwent an identical assay protocol. NIH3T3 and CHO have been previously shown to express both 5-HT$_{2A}$ and 5-HT$_{1B}$ receptors (Giles et al., 1996, *Br J Pharmacol,* 117 (6):1119-1126; Saucier and Albert, 1997, *J Neurochem,* 68(5):1998-2011). However, the expression level of endogenous receptors in these cell lines is sufficiently low so as not to interfere with the study of recombinant receptors whose expression levels are generally significantly higher. Higher fluorescence intensities were observed for both canine and human 5-HT$_{2A}$ compared to the canine and human 5-HT$_{2B}$ receptors. A slightly higher fluorescence intensity peak was observed for the human 5-HT$_{2A}$ receptor compared to the canine 5-HT$_{2A}$ (15800 vs. 13600 peak fluorescence intensity units; FIG. 5A). A weaker response was observed for the canine 5-HT$_{2B}$ receptor (peak fluorescence intensity=3500 units) compared to the human 5-HT$_{2B}$ receptor (peak fluorescence intensity=5000 units; FIG. 5B). Saturation binding analysis using [$^3$H]5-HT was performed on membranes prepared from HEK-293 cells transfected with the canine 5-HT$_{2B}$ and demonstrated that the expression level ($B_{max}$ approximately 1 pmol/mg protein) was lower compared to the expression level obtained in membranes prepared from CHO cells expressing human 5-HT$_{2B}$ ($B_{max}$ approximately 36 fmol/mg protein). To further address the difference in peak fluorescence intensity between the human and canine 5-HT$_{2B}$ receptor, the 5-HT stimulated $Ca^{2+}$ response experiment was repeated but using the same cell line background (HEK-293) for both human and canine 5-HT$_{2A}$ and 5-HT$_{2B}$ receptors (canine 5-HT$_{2A}$, $B_{max}$ approximately 0.7 pmol/mg protein; human 5-HT$_{2A}$, $B_{max}$ approximately 0.9 pmol/mg protein; canine 5-HT$_{2B}$, $B_{max}$ approximately 1 pmol/mg protein; human 5-HT$_{2B}$, $B_{max}$ approximately 0.8 pmol/mg protein). A significantly higher fluorescence intensity peak after 5-HT stimulation was observed for the human 5-HT$_{2B}$ receptor compared to the canine 5-HT$_{2B}$ receptor, whereas the human 5-HT$_{2A}$ and canine 5-HT$_{2A}$ receptors were within the same range.

The activities of various other 5-HT$_2$ receptor agonists exhibiting a range of potencies and relative efficacies are summarized in Table 3 below. The affinities of the antagonists are summarized in Table 4 below. The rank order of potency and antagonist affinities were consistent with the established pharmacology.

TABLE 3

Agonist potency and relative efficacy at cloned canine (c) and human (h) 5-HT$_{2A}$ and 5-HT$_{2B}$ receptors.

| | c5-HT$_{2A}$ | | h5-HT$_{2A}$ | | c5-HT$_{2B}$ | | h5-HT$_{2B}$ | |
|---|---|---|---|---|---|---|---|---|
| | HEK-293 | | NIH3T3 | | HEK-293 | | CHO | |
| Compound | pIC$_{50}$ | Rel. eff. | pIC$_{50}$ | Rel. eff. | pIC$_{50}$ | Rel. eff. | pIC$_{50}$ | Rel. eff |
| 5-HT | 7.70 ± 0.46 | 1 | 7.38 ± 0.46 | 1 | 8.36 ± 0.19 | 1 | 8.73 ± 0.23 | 1 |
| DOI | 8.98 ± 0.09 | 0.89 ± 0.02 | 8.48 ± 0.09 | 0.65 ± 0.04 | 8.10 ± 0.20 | 0.75 ± 0.03 | 8.75 ± 0.19 | 0.96 ± 0.02 |
| m-CPP | 7.57 ± 0.11 | 0.71 ± 0.04 | 6.70 ± 0.05 | 0.20 ± 0.02 | IA | | 8.35 ± 0.15 | 0.55 ± 0.06 |
| SCH-23390 | 6.68 ± 0.10 | 0.61 ± 0.03 | 7.58 ± 0.22 | 0.17 ± 0.02 | 5.88 ± 0.87 | 0.37 ± 0.05 | 7.10 ± 0.16 | 0.66 ± 0.05 |
| α-Me-5-HT | 8.20 ± 0.60 | 1.06 ± 0.05 | 7.58 ± 0.13 | 0.91 ± 0.02 | 8.80 ± 0.36 | 0.77 ± 0.01 | 8.75 ± 0.17 | 0.84 ± 0.01 |
| BW-723C86 | 7.48 ± 0.13 | 0.89 ± 0.03 | 6.60 ± 0.07 | 0.56 ± 0.03 | 8.14 ± 0.14 | 0.93 ± 0.03 | 9.03 ± 0.06 | 0.98 ± 0.01 |
| TFMPP | 7.37 ± 0.13 | 0.72 ± 0.04 | 6.63 ± 0.28 | 0.17 ± 0.01 | IA | | 7.90 ± 0.21 | 0.49 ± 0.04 |
| 5-CT | 7.70 ± 0.13 | 0.94 ± 0.08 | 6.80 ± 0.09 | 0.70 ± 0.13 | 8.00 ± 0.15 | 1.19 ± 0.05 | 8.85 ± 0.18 | 0.95 ± 0.01 | pEC$_{50}$ values are the mean ± S.E.M of 3 to 6 independent experiments.
Relative efficacy (Rel. eff.) values are the corresponding fraction of the response elicited by the compounds compared to the response elicited by 10 μM 5-HT.
ND: not determined;
IA: inactive.

TABLE 4

Antagonist affinities (pK$_B$) at cloned canine and human 5-HT$_{2A}$ and 5-HT$_{2B}$ receptors. Data are the mean ± S.E.M of 3 to 6 experiments.

| | Receptor: | | | |
|---|---|---|---|---|
| | c5-HT$_{2A}$ | h5-HT$_{2A}$ | c5-HT$_{2B}$ | h5-HT$_{2B}$ |
| | Cell Line: | | | |
| Compound | HEK-293 | NIH3T3 | HEK-293 | CHO |
| Ritanserin | 8.15 ± 0.19 | 7.98 ± 0.22 | 8.00 ± 0.41 | 8.23 ± 0.22 |
| Risperidone | 9.68 ± 0.11 | 9.13 ± 0.22 | 8.40 ± 0.97 | 7.25 ± 0.14 |
| MDL-100907 | 9.38 ± 0.06 | 8.88 ± 0.03 | <5 | <5 |
| Eplivanserin | 9.60 ± 0.49 | 9.43 ± 0.03 | <5 | <5 |
| SB-204741 | <5 | <5 | 7.35 ± 0.45 | 7.35 ± 0.76 |
| Mesulergine | 7.60 ± 0.10 | 7.23 ± 0.13 | 9.30 ± 0.45 | 8.63 ± 0.07 |
| Yohimbine | <5 | <5 | 8.80 ± 0.43 | 7.35 ± 0.45 |
| Methiothepin | 8.33 ± 0.09 | 7.30 ± 0.10 | 8.07 ± 0.77 | 8.28 ± 0.03 |
| Ketanserin | 8.90 ± 0.13 | 8.53 ± 0.48 | 5.80 ± 0.40 | <5 |
| Olanzapine | 7.27 ± 0.15 | 6.93 ± 0.03 | 6.60 ± 0.13 | 7.43 ± 0.19 |

For the canine 5-HT$_{2A}$ receptor, several compounds were found to display higher potencies compared to their potencies for the human 5-HT$_{2A}$ (e.g., mCPP, SCH-23390, TFMPP, BW-723C86 and 5-CT). Similarly, most of these compounds had higher relative efficacies on the canine 5-HT$_{2A}$ receptor compared to the human 5-HT$_{2A}$ receptor. In general, all the antagonists had similar affinities for the human and canine 5-HT$_{2A}$ receptors except methiothepin, which displayed an eleven-fold higher affinity for the canine 5-HT$_{2A}$ receptor compared to the human 5-HT$_{2A}$ receptor. For the 5-HT$_{2B}$ receptor, several agonists were found to display lower potencies on the canine 5-HT$_{2B}$ receptor compared to the human 5-HT$_{2B}$ receptor. These compounds had lower relative efficacies on the canine 5-HT$_{2B}$ receptor compared to the human 5-HT$_{2B}$ receptor. For mCPP and TFMPP, no agonistic response was observed on canine 5-HT$_{2B}$ receptor.

None of the compounds (10 μM) tested elicited a response in non-transfected cells (HEK-293, NIH3T3 or CHO). In addition, none of the antagonists tested increased Ca$^{2+}$ in any of the transfected cell types.

Example 4

Analysis of Tissue Distribution of Canine 5-HT$_{2A}$ and 5-HT$_{2B}$ Receptor mRNA Expression Total RNA from different dog tissues (Beagle, Bioreclamation Inc., Hicksville, N.Y.) was isolated using Trizol (Invitrogen), and treated with DNAse (Epicentre Technologies, Madison) to remove genomic DNA. cDNA was synthesized from 3 μg of total RNA of each tissue using SuperScript III RT (Invitrogen) with 100 ng oligo dT$_{18-21}$ (Amersham Biosciences, United Kingdom). The reaction was incubated at 50° C. for 30 minutes, then heat-inactivated at 80° C. for three minutes and chilled on ice. The cDNA was diluted 30-fold and 2 μl of each sample was analyzed by quantitative PCR using the SmartCycler (Cepheid, Sunnyvale, Calif.) in quadruplicates. The PCR mix consisted of 0.2× Sybr Green I (Invitrogen, Carlsbad, Calif.), 10 mM Tris-HCl pH 8.8, 50 mM KCl, 1 unit TaqStart Antibody (Becton Dickinson, Palo Alto, Calif.), 3 units of AmpliTaq DNA polymerase, 200 mM Trehalose (Sigma) and 200 μM dNTPs (Amersham). PCR primers were from GenBase (San Diego, Calif.). Standard curves were generated for each gene by dilution of linearized plasmids containing an insert for the gene of interest (canine 5-HT$_{2A}$ forward primer (SEQ ID NO.:11): TGGATCGGT-TACCTCTCCTC; canine 5-HT$_{2A}$ reverse primer (SEQ ID NO.:12): GGCCGGTATAGTGTTCACTA; canine 5-HT$_{2B}$ forward primer (SEQ ID NO.:13): ACAGTGGGCAGCTCT-TCTGA; canine 5-HT$_{2B}$ reverse primer (SEQ ID NO.:14): CCAACTAGCAGATCAGCCAC), or of PCR products generated by a primer pair straddling the primer pair used for quantitation (B-Actin). PCR cycle parameters were the following: initial hold at 95° C. for 90 sec, 40 cycles of 95° C. for 5 sec, 62° C.-70° C. (depending on primer pair) for 7 sec, and 72° C. for 15 sec. At the end a melt curve analysis was performed.

Figure 6:
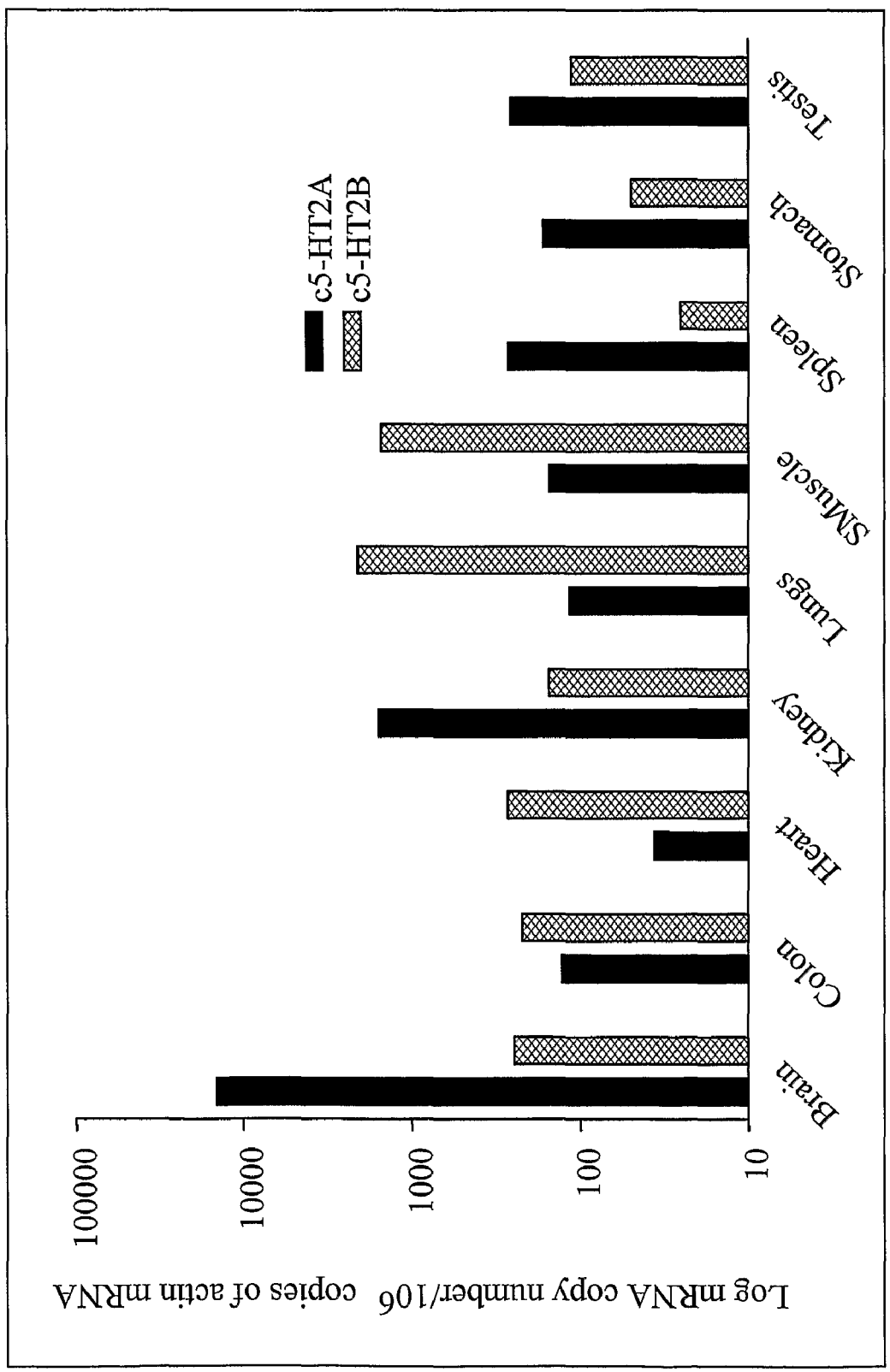
FIG. 6 depicts the detection of canine 5-HT$_{2A}$ and c5-HT$_{2B}$ receptor mRNA in various canine tissues by quantitative RT-PCR. Quantitative PCR analyses were performed to measure the relative abundance of canine 5-HT$_{2A}$ and canine 5-HT$_{2B}$ receptor mRNA from 9 different canine tissues, respectively. In parallel, PCR measurements for beta actin gene expression in different tissues served as internal controls. The relative canine 5-HT$_{2A}$ and canine 5-HT$_{2B}$ mRNA expression levels were normalized to the actin expression levels for each tissue, respectively.

The quantitative expression profiles of canine 5-HT$_{2A}$ and canine 5-HT$_{2B}$ receptors are shown in FIG. 6. The canine 5-HT$_{2A}$ receptor was detected mainly in brain and at much lower levels in peripheral tissues, whereas the canine 5-HT$_{2B}$ receptor was detected mainly in lungs and smooth muscles and at lower level in brain.

The following order of expression levels was observed for canine 5-HT$_{2A}$ receptor mRNA: brain>>kidney>spleen>testis>stomach>smooth muscle>colon>lungs>heart. The following order of expression levels was observed for canine 5-HT$_{2B}$ receptor mRNA: lungs>smooth muscle>heart>brain>colon>kidney>testis>stomach>spleen.

What is claimed is:

1. An isolated biologically active canine 5-hydroxytryptamine 2 receptor polypeptide having an amino acid sequence as set forth in SEQ ID NO.:8.

* * * * *

SEQUENCE LISTING

<160> NUMBER OF SEQ ID NOS: 14

<210> SEQ ID NO 1
<211> LENGTH: 30
<212> TYPE: DNA
<213> ORGANISM: Artificial
<220> FEATURE:
<223> OTHER INFORMATION: Canine 5-HT2A forward RACE primer

<400> SEQUENCE: 1
tctagcgaga tggcgcacag gtgcatgatg                                    30

<210> SEQ ID NO 2
<211> LENGTH: 30
<212> TYPE: DNA
<213> ORGANISM: Artificial
<220> FEATURE:
<223> OTHER INFORMATION: Canine 5-HT2A reverse RACE primer

<400> SEQUENCE: 2
ccaccttgtg tgtgagtgat cctggcacac                                    30

<210> SEQ ID NO 3
<211> LENGTH: 45
<212> TYPE: DNA
<213> ORGANISM: Artificial
<220> FEATURE:
<223> OTHER INFORMATION: Canine 5-HT2A forward primer

<400> SEQUENCE: 3
actagactcg aggccaccat ggatgtcctc tttgaggata atgct                   45

<210> SEQ ID NO 4
<211> LENGTH: 44
<212> TYPE: DNA
<213> ORGANISM: Artificial
<220> FEATURE:
<223> OTHER INFORMATION: Canine 5-HT2A reverse primer

<400> SEQUENCE: 4
actagagcgg ccgctcacac acagctaacc ttttcattca ctgt                         44

<210> SEQ ID NO 5
<211> LENGTH: 46
<212> TYPE: DNA
<213> ORGANISM: Artificial
<220> FEATURE:
<223> OTHER INFORMATION: Canine 5-HT2B forward primer

<400> SEQUENCE: 5
agtagagaat cgccaccat ggccatctct tatagaatat cagaac                        46

<210> SEQ ID NO 6
<211> LENGTH: 41
<212> TYPE: DNA
<213> ORGANISM: Artificial
<220> FEATURE:
<223> OTHER INFORMATION: Canine 5-HT2B reverse primer

<400> SEQUENCE: 6
actagagcgg ccgcattagg tgaatacctc tattccttct a                            41

<210> SEQ ID NO 7
<211> LENGTH: 1413
<212> TYPE: DNA
<213> ORGANISM: Canine

<400> SEQUENCE: 7

| | |
|---|---:|
| atggatgtcc tctttgagga taatgctcct ttgagcccaa ccaccagctc cttaatgccg | 60 |
| tcaaacgggg acccaaggct ctacggcaac gacctgaacg ctggagacgc gaacacttcg | 120 |
| gatgcattta actggacagt ggatgcagaa aaccgaacca acctttcctg cgagggctgt | 180 |
| ctctcgccac catgcttctc cctacttcat ctccaggaaa aaactggtc ggctctgttg | 240 |
| acagcggtcg tgattattct gaccattgct ggaaacatac tcgtcatcat ggcagtgtcc | 300 |
| ctagagaaaa agctgcagaa cgccaccaac tatttcctga tgtcacttgc atagctgat | 360 |
| atgctgctgg gtttccttgt catgcccgtg tccatgctaa ccatcctata tggttaccgg | 420 |
| tggcctctgc ctagcaaact gtgcgccgtg tggatctacc tggacgtgct cttctccacg | 480 |
| gcctccatca tgcacctgtg cgccatctcg ctagaccgct acgttgccat ccagaacccc | 540 |
| atccaccata gccgattcaa ctccagaact aaggcatttc tgaagatcat cgctgtctgg | 600 |
| accatatcag tgggtatatc tatgccaata ccagttttcg ggctacagga tgattccaag | 660 |
| gtctttaagg aagggagctg cctacttgcc gacgataact tgtcctgat cggctctttc | 720 |
| gtgtcgttct tcattccctt aaccatcatg gtgatcacct actttctaac tatcaagtcg | 780 |
| ctccagaaag aagccacctt gtgtgtgagt gatcctggca cacgggccaa gctagcgtct | 840 |
| ttcagcttcc tccctcagag ctccctgtct tcggaaaagc tcttcaacg atcaatccac | 900 |
| agggagccag gtcctacgg caggaggact atgcagtcca tcagcaatga gcagaaagct | 960 |
| tgcaaggtgc tgggcattgt cttcttcctg tttgtggtga tgtggtgccc attcttcatc | 1020 |

```
acgaacataa tggccgtcat ctgcaaagag tcctgcaacg aggatatcat tggagccctg      1080
ctcaacgtgt ttgtctggat cggttacctc tcctcggcgg tcaacccact ggtatacaca      1140
ctgttcaaca agacctacag gtcggccttc tcccggtata ttcagtgtca gtacaaggaa      1200
aataaaaaac cattgcagtt aattttagtg aacactatac cggccttggc ctacaaatct      1260
agtcaactcc aaatgggaca aaaaaagaat tcaagaaag atgccaagag cacagataat       1320
gactacagca tggttgctct aggaaaacaa cattcagaag acgctcctac agacaatatt      1380
aacacagtga atgaaaaggt tagctgtgtg tga                                   1413
```

```
<210> SEQ ID NO 8
<211> LENGTH: 470
<212> TYPE: PRT
<213> ORGANISM: Canine

<400> SEQUENCE: 8
```

```
Met Asp Val Leu Phe Glu Asp Asn Ala Pro Leu Ser Pro Thr Thr Ser
 1               5                  10                  15

Ser Leu Met Pro Ser Asn Gly Asp Pro Arg Leu Tyr Gly Asn Asp Leu
             20                  25                  30

Asn Ala Gly Asp Ala Asn Thr Ser Asp Ala Phe Asn Trp Thr Val Asp
         35                  40                  45

Ala Glu Asn Arg Thr Asn Leu Ser Cys Glu Gly Cys Leu Ser Pro Pro
     50                  55                  60

Cys Phe Ser Leu Leu His Leu Gln Glu Lys Asn Trp Ser Ala Leu Leu
 65                  70                  75                  80

Thr Ala Val Val Ile Ile Leu Thr Ile Ala Gly Asn Ile Leu Val Ile
                 85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190

Phe Leu Lys Ile Ile Ala Val Trp Thr Ile Ser Val Gly Ile Ser Met
        195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Ser Leu Gln Lys Glu Ala Thr Leu Cys Val Ser Asp Pro
            260                 265                 270

Gly Thr Arg Ala Lys Leu Ala Ser Phe Ser Phe Leu Pro Gln Ser Ser
        275                 280                 285

Leu Ser Ser Glu Lys Leu Phe Gln Arg Ser Ile His Arg Glu Pro Gly
    290                 295                 300
```

-continued

```
Ser Tyr Gly Arg Arg Thr Met Gln Ser Ile Ser Asn Glu Gln Lys Ala
305                 310                 315                 320

Cys Lys Val Leu Gly Ile Val Phe Phe Leu Phe Val Val Met Trp Cys
            325                 330                 335

Pro Phe Phe Ile Thr Asn Ile Met Ala Val Ile Cys Lys Glu Ser Cys
            340                 345                 350

Asn Glu Asp Ile Ile Gly Ala Leu Leu Asn Val Phe Val Trp Ile Gly
        355                 360                 365

Tyr Leu Ser Ser Ala Val Asn Pro Leu Val Tyr Thr Leu Phe Asn Lys
    370                 375                 380

Thr Tyr Arg Ser Ala Phe Ser Arg Tyr Ile Gln Cys Gln Tyr Lys Glu
385                 390                 395                 400

Asn Lys Lys Pro Leu Gln Leu Ile Leu Val Asn Thr Ile Pro Ala Leu
            405                 410                 415

Ala Tyr Lys Ser Ser Gln Leu Gln Met Gly Gln Lys Lys Asn Ser Lys
            420                 425                 430

Lys Asp Ala Lys Ser Thr Asp Asn Asp Tyr Ser Met Val Ala Leu Gly
        435                 440                 445

Lys Gln His Ser Glu Asp Ala Pro Thr Asp Asn Ile Asn Thr Val Asn
    450                 455                 460

Glu Lys Val Ser Cys Val
465                 470

<210> SEQ ID NO 9
<211> LENGTH: 1305
<212> TYPE: DNA
<213> ORGANISM: Artificial
<220> FEATURE:
<223> OTHER INFORMATION: Canine 5-hydroxytryptamine 2B coding sequence

<400> SEQUENCE: 9
atggccatct cttatagaat atcagaacag agcacaattc ctgagcacat tttgcagagc      60
tcctttcatc acttaatctt tgctaactgg tctggattac aaacagaatc gataccagag     120
gaaatgaaac agactggtga gcaacaggga agaaaccac agtgggcagc tcttctgata     180
ctcacggtga taatacccac aattggtggg aacatcctgg ttattctggc tatttcactg     240
gaaaaaaagc tgcagtatgc taccaattat tttctaatgt ccctagcagt ggctgatctg     300
ctagttggat tgtttgtgat gccgattgcc cttttgacaa taatgtttga gactatatgg     360
cccctcccac ttgttctatg ccctgcctgg ttatttcttg atgttctttt ctctactgca     420
tccatcatgc atctctgtgc catttctgtg gatcgttata tagccatcaa aaagccaatc     480
caggccaatc aaagtaactc acgagctaca gcattcatca agattacagt ggtatggtta     540
atttcaatag gcattgccat tccagtccct attagaggga tagaaactga tcggagtaac     600
ccaagcaaca tcacctgtgt gctgacaaag gatcgttttg caacttcat gctgtatggc     660 tcactggctg ccttttttac acctctggca atcatgattg tcacctactt tctcactatc     720
cgtgctttac agaagaaagc ttccttggtc aaaaacaagc cacctccatg cctaacatgg     780
ctgactgtgt ctacagcttt ccgaaggaat gaaacacctt gctcgtcacc tgaaaaggtg     840
gcaatgctgg atggttccca caagacaga actctgccca gctcaagtga tgacctactt     900
atgcgaagaa tgtccacagc tggaaaaaag tccatgcaga cctttccaa cgaacagaga     960 gcctccaagg ttctagggat tgttttttttt ctcttttttgc ttatgtggtg tcccttttt    1020 attacaaatg taactttagt tttgtgtgat tcctgcaacc agactactct caatatgctt    1080
```

```
ctggaggtat tgtgtgtggat aggctatgtt tcctcaggag taaatccttt ggtttacacc    1140
ctcttcaata aaacatttcg gaatgcattt ggccgatata ttacctgcaa ttaccaggcc    1200
atgaaatcag taaaaactgt cagaaaatgc tccagcaata actacttccg aaatggcaga    1260
gaactcaaag ttttttcatga aacgtggaat gtgaaatggt attaa                   1305
```

<210> SEQ ID NO 10
<211> LENGTH: 434
<212> TYPE: PRT
<213> ORGANISM: Canine

<400> SEQUENCE: 10

```
Met Ala Ile Ser Tyr Arg Ile Ser Glu Gln Ser Thr Ile Pro Glu His
1               5                   10                  15

Ile Leu Gln Ser Ser Phe His His Leu Ile Phe Ala Asn Trp Ser Gly
                20                  25                  30

Leu Gln Thr Glu Ser Ile Pro Glu Glu Met Lys Gln Thr Gly Glu Gln
            35                  40                  45

Gln Gly Lys Lys Pro Gln Trp Ala Ala Leu Leu Ile Leu Thr Val Ile
        50                  55                  60

Ile Pro Thr Ile Gly Gly Asn Ile Leu Val Ile Leu Ala Ile Ser Leu
65                  70                  75                  80

Glu Lys Lys Leu Gln Tyr Ala Thr Asn Tyr Phe Leu Met Ser Leu Ala
                85                  90                  95

Val Ala Asp Leu Leu Val Gly Leu Phe Val Met Pro Ile Ala Leu Leu
                100                 105                 110

Thr Ile Met Phe Glu Thr Ile Trp Pro Leu Pro Leu Val Leu Cys Pro
            115                 120                 125

Ala Trp Leu Phe Leu Asp Val Leu Phe Ser Thr Ala Ser Ile Met His
        130                 135                 140

Leu Cys Ala Ile Ser Val Asp Arg Tyr Ile Ala Ile Lys Lys Pro Ile
145                 150                 155                 160

Gln Ala Asn Gln Ser Asn Ser Arg Ala Thr Ala Phe Ile Lys Ile Thr
                165                 170                 175

Val Val Trp Leu Ile Ser Ile Gly Ile Ala Ile Pro Val Pro Ile Arg
            180                 185                 190

Gly Ile Glu Thr Asp Arg Ser Asn Pro Ser Asn Ile Thr Cys Val Leu
        195                 200                 205

Thr Lys Asp Arg Phe Gly Asn Phe Met Leu Tyr Gly Ser Leu Ala Ala
210                 215                 220

Phe Phe Thr Pro Leu Ala Ile Met Ile Val Thr Tyr Phe Leu Thr Ile
225                 230                 235                 240

Arg Ala Leu Gln Lys Lys Ala Ser Leu Val Lys Asn Lys Pro Pro Pro
                245                 250                 255

Cys Leu Thr Trp Leu Thr Val Ser Thr Ala Phe Arg Arg Asn Glu Thr
            260                 265                 270

Pro Cys Ser Ser Pro Glu Lys Val Ala Met Leu Asp Gly Ser His Lys
        275                 280                 285

Asp Arg Thr Leu Pro Ser Ser Asp Asp Leu Leu Met Arg Arg Met
        290                 295                 300

Ser Thr Ala Gly Lys Lys Ser Met Gln Thr Ile Ser Asn Glu Gln Arg
305                 310                 315                 320

Ala Ser Lys Val Leu Gly Ile Val Phe Phe Leu Phe Leu Leu Met Trp
                325                 330                 335
```

-continued

```
Cys Pro Phe Phe Ile Thr Asn Val Thr Leu Val Leu Cys Asp Ser Cys
            340                 345                 350

Asn Gln Thr Thr Leu Asn Met Leu Leu Glu Val Phe Val Trp Ile Gly
        355                 360                 365

Tyr Val Ser Ser Gly Val Asn Pro Leu Val Tyr Thr Leu Phe Asn Lys
    370                 375                 380

Thr Phe Arg Asn Ala Phe Gly Arg Tyr Ile Thr Cys Asn Tyr Gln Ala
385                 390                 395                 400

Met Lys Ser Val Lys Thr Val Arg Lys Cys Ser Ser Asn Asn Tyr Phe
                405                 410                 415

Arg Asn Gly Arg Glu Leu Lys Val Phe His Glu Thr Trp Asn Val Lys
                420                 425                 430

Trp Tyr

<210> SEQ ID NO 11
<211> LENGTH: 20
<212> TYPE: DNA
<213> ORGANISM: Artificial
<220> FEATURE:
<223> OTHER INFORMATION: Canine 5-HT2A quantitative PCR forward primer

<400> SEQUENCE: 11
tggatcggtt acctctcctc                                              20

<210> SEQ ID NO 12
<211> LENGTH: 20
<212> TYPE: DNA
<213> ORGANISM: Artificial
<220> FEATURE:
<223> OTHER INFORMATION: Canine 5-HT2A quantitative PCR reverse primer

<400> SEQUENCE: 12
ggccggtata gtgttcacta                                              20

<210> SEQ ID NO 13
<211> LENGTH: 20
<212> TYPE: DNA
<213> ORGANISM: Artificial
<220> FEATURE:
<223> OTHER INFORMATION: Canine 5-HT2B quantitative PCR forward primer

<400> SEQUENCE: 13
acagtgggca gctcttctga                                              20

<210> SEQ ID NO 14
<211> LENGTH: 20
<212> TYPE: DNA
<213> ORGANISM: Artificial
<220> FEATURE:
<223> OTHER INFORMATION: Canine 5-HT2B quantitative PCR reverse primer

<400> SEQUENCE: 14
ccaactagca gatcagccac                                              20
```